(12) United States Patent
Walsh et al.

(10) Patent No.: US 8,977,085 B2
(45) Date of Patent: Mar. 10, 2015

(54) SURFACE STRUCTURE MODIFICATION

(75) Inventors: Laurence James Walsh, Ferny Hills (AU); Roy George, Southport (AU)

(73) Assignee: The University of Queensland, Queensland (AU)

( * ) Notice: Subject to any disclaimer, the term of this patent is extended or adjusted under 35 U.S.C. 154(b) by 741 days.

(21) Appl. No.: 13/127,453

(22) PCT Filed: Nov. 3, 2009

(86) PCT No.: PCT/AU2009/001430
§ 371 (c)(1),
(2), (4) Date: May 3, 2011

(87) PCT Pub. No.: WO2010/051579
PCT Pub. Date: May 14, 2010

(65) Prior Publication Data
US 2011/0217665 A1    Sep. 8, 2011

(30) Foreign Application Priority Data

Nov. 4, 2008  (AU) ................................ 2008905687

(51) Int. Cl.
| | |
|---|---|
| G02B 6/26 | (2006.01) |
| C03C 25/62 | (2006.01) |
| C03C 25/68 | (2006.01) |
| A61C 1/00 | (2006.01) |
| G01N 21/64 | (2006.01) |

(52) U.S. Cl.
CPC .............. *G02B 6/262* (2013.01); *C03C 25/626* (2013.01); *C03C 25/68* (2013.01); *A61C 1/0046* (2013.01); *G01N 21/64* (2013.01)
USPC .................................. 385/38; 385/31; 385/43

(58) Field of Classification Search
None
See application file for complete search history.

(56) References Cited

U.S. PATENT DOCUMENTS

| | | | |
|---|---|---|---|
| 3,801,389 A | 4/1974 | Fujimura | |
| 5,651,783 A | 7/1997 | Reynard | |
| 5,668,902 A * | 9/1997 | Kurata | ............................ 385/38 |
| 5,707,368 A | 1/1998 | Cozean et al. | |
| 5,812,722 A * | 9/1998 | Anazawa et al. | ............. 385/123 |
| 5,859,937 A * | 1/1999 | Nomura | ......................... 385/12 |
| 6,004,315 A * | 12/1999 | Dumont | ......................... 606/15 |
| 6,251,103 B1 | 6/2001 | Berlin | |
| 6,416,390 B1 | 7/2002 | Mezei et al. | |
| 6,905,627 B2 | 6/2005 | Wei et al. | |
| 7,099,552 B1 | 8/2006 | Oron et al. | |
| 7,306,459 B1 | 12/2007 | Williams et al. | |
| 2003/0199860 A1 | 10/2003 | Loeb et al. | |

(Continued)

FOREIGN PATENT DOCUMENTS

| | | |
|---|---|---|
| CA | 2207570 | 12/1997 |
| CA | 2265565 | 3/1998 |

(Continued)

OTHER PUBLICATIONS

International Search Report, PCT/AU2009/001430, mailed Feb. 9, 2010.
Fujii, H. et al., "Light Scattering Properties of a Rough-Ended Optical Fibre," Optics and Laser Technology, Feb. 1984, pp. 40-44.

*Primary Examiner* — Michelle R Connelly
(74) *Attorney, Agent, or Firm* — Nixon & Vanderhye PC

(57) ABSTRACT

A method of forming an optical fiber tip, the method including, roughening at least part of an end portion of the optical fiber; and, etching the roughed end portion to thereby form an optical fiber tip.

22 Claims, 17 Drawing Sheets

(56) References Cited

U.S. PATENT DOCUMENTS

| | | |
|---|---|---|
| 2004/0134884 A1 | 7/2004 | Wei et al. |
| 2006/0188212 A1 | 8/2006 | Oron et al. |
| 2008/0121614 A1* | 5/2008 | Mitsui et al. .................... 216/24 |
| 2008/0317429 A1* | 12/2008 | Boutoussov et al. ......... 385/146 |

FOREIGN PATENT DOCUMENTS

| | | | |
|---|---|---|---|
| CA | 2 650 707 | | 11/2007 |
| CA | 2 682 397 | | 11/2008 |
| GB | 1558689 A | * | 1/1980 |
| WO | 8903202 A2 | | 4/1989 |

* cited by examiner

Fig. 10A				Fig. 10B
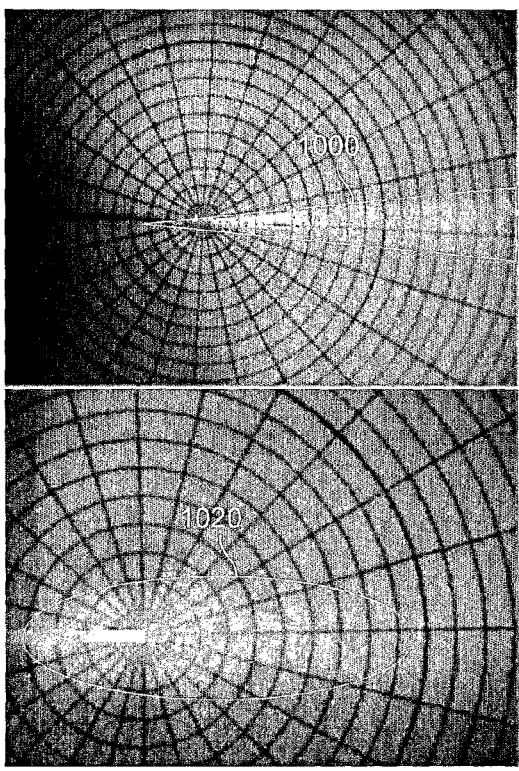
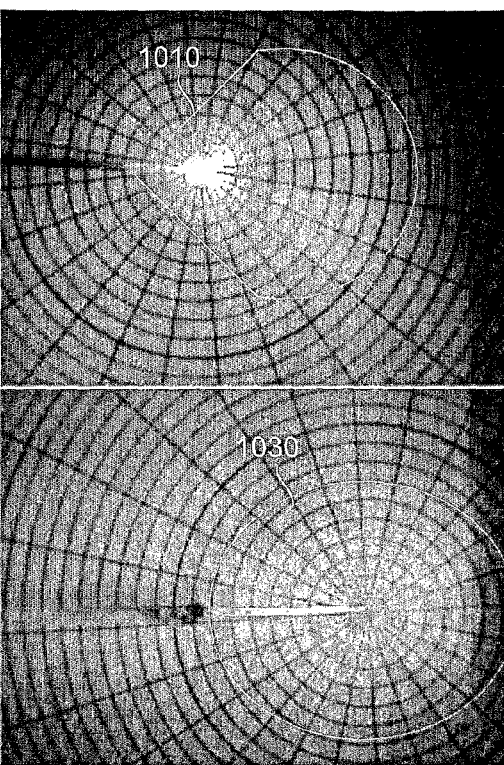
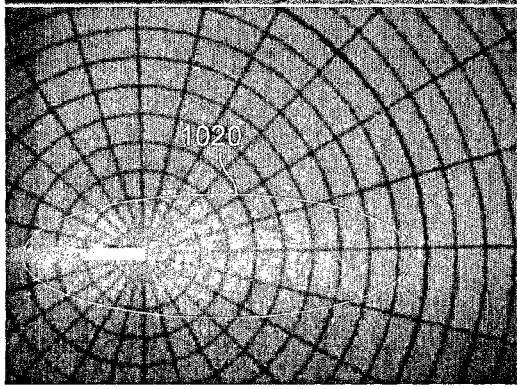
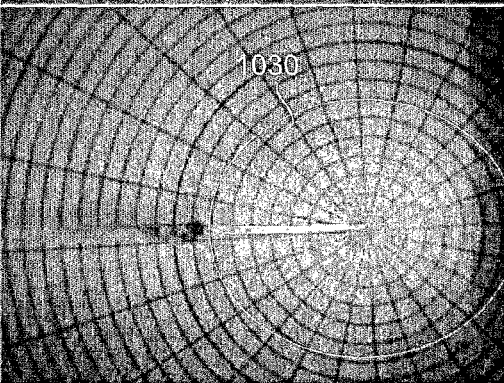
Fig. 10C				Fig. 10D

SURFACE STRUCTURE MODIFICATION

BACKGROUND OF THE INVENTION

The present invention relates to a method of modifying the surface structure of a material and in particular for forming an optical fibre tip suitable for emitting or detecting radiation. The present invention also relates to a method and apparatus for interaction with a part of a subject and in particular using an optical fibre tip for emitting or detecting radiation.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Optical fibres are used in a range of different medical applications, typically for delivery of laser or other similar radiation to part of a subject, or for detecting radiation, such as fluorescence. In dentistry, radiation is used for the identification of caries, plaque and bacterial infection on teeth.

U.S. Pat. Nos. 5,306,144, 6,024,562 and 6,186,780 in the name of Hibst et al. and assigned to Kaltenbach & Voigt GmbH & Co., disclose optical methods and devices for detecting dental caries, plaque and bacterial infections on teeth using visible red light from a laser which induces fluorescence. However, these techniques do not allow for the identification of bacterial infection within the pulp chambers and root canals of teeth.

U.S. Pat. No. 5,503,559 in the name of Vari and assigned to Cedars-Sinai Medical Center, discloses a fibre optic endodontic method and apparatus for locating the entrance of the root canal using induced fluorescence spectroscopy and subsequently sealing and filling the root canal using a light-cured restorative. However, this method and apparatus does not identify the presence location or extent of the bacterial infection in the root canal, nor does it provide a controlled means for eliminating that infection at the time of treatment.

A commercially available laser fluorescence emission and detection device commonly referred to as the DiagnoDENT®, uses a diode laser which emits visible laser radiation at a wavelength of 655 nm, and optical tips with a central emitting fibre and a plurality of peripheral collecting fibres. The complex multi-element rigid optical tips typically employed with this device for detecting dental caries are unsuitable for use in the pulp chamber and root canal space because of their large diameter and length, and lack of flexibility.

A known method of treatment of root canal microbial infection is photo-activated disinfection (PAD), a photodynamic process which utilises low power radiation from a diode laser, which is typically transmitted through a disposable optical fibre to activate a sensitizing agent within an aqueous solution. U.S. Pat. No. 5,611,793 by Wilson and Wilson teaches a method of using PAD for disinfecting or sterilizing tissues of the oral cavity or a wound or lesion in the oral cavity using a photosensitizing compound irradiated with laser light.

Lasers are also used for smear layer removal and root canal preparation, as well as for soft tissue applications such as pulp capping and pulpotomy. For the endodontic hard tissue applications, delivery of laser energy is typically undertaken using plain optical fibres attached to dental handpieces.

Optical fibres in endodontics need to be small and flexible so as to negotiate the complex curved and tortuous anatomy of the root canal. Flexibility of existing optical fibres is less than for the super-elastic Ni—Ti instruments used in conventional endodontics. More importantly, existing fibres have plain ends, so the laser energy exits forward with a relatively small divergence, requiring the clinician to move the fibre in a plunging, withdrawing and rotating action to attempt to gain even irradiation of the canal walls.

A number of modifications for optical fibres for medical applications have been reported in Verdaasdonk R M, van Swol C F. Laser light delivery systems for medical applications. Phys Med Biol 1997; 42 (5):869-894.

For dentistry, such modifications include hollow waveguide extensions to optical fibres for Er:YAG lasers Alves P R, Aranha N, Alfredo E, Marchesan M A, Brugnera Junior A, Sousa-Neto M D. *"Evaluation of hollow fibreoptic tips for the conduction of Er:YAG laser"*. Photomed Laser Surg 2005; 23 (4):410-415, and the use of hollow metal conical tips with slits for lateral emission Stabholz A, Zeltser R, Sela M, Peretz B, Moshonov J, Ziskind D, Stabholz A. *"The use of lasers in dentistry: principles of operation and clinical applications"*. Compend Contin Educ Dent 2003; 24 (12):935-948. Such metal waveguides have limited clinical use in situations other than in large and straight root canals because of their size and inherent rigidity.

For optical fibres, conical ends can be created by grinding and polishing as described in Shirk G J, Gimpelson R J, Krewer K *"Comparison of tissue effects with sculptured fibreoptic cables and other Nd:YAG laser and argon laser treatments"*. Lasers Surg Med 1991; 11 (6):563-568, and Shoji S, Hariu H, Horiuchi H *"Canal enlargement by Er:YAG laser using a cone-shaped irradiation tip"*. J Endod 2000; 26 (8): 454-458.

The ends of optical fibres can also be modified by fixing certain materials to the fibre end to disperse the energy, including titanium dioxide. Such isotropic tips may have application for photodynamic therapy (photo-activated disinfection) in endodontics, as described in Walsh L J. "The current status of laser applications in dentistry". Aust Dent J 2003; 48 (3):146-155.

However, even with the use of conical ends, and tips modified will fixing materials, the majority of emissions are generally from the end of the fibre. Consequently, such configurations require significant manipulation by the operator to attempt to evenly irradiate or otherwise expose the cavity to radiation. This in turn renders the process time consuming will only a limited guarantee of success. It is therefore apparent it that current fibre optics are unsuitable for use in orthodontic applications.

Optical fibres can also be used in other medical applications, such as photodynamic therapy (PDT), which is a minimally invasive treatment used in treating malignant disease.

*"Photodynamic therapy: a clinical reality in the treatment of cancer"* LANCET Oncology Vol 1 December 2000 by Colin Hopper, describes using oxygen, a photosensitiser, and radiation to perform PDT. In this document, laser light is directed along fibreoptic cables, allowing light to be introduced into hollow organs and deep-seated tumours.

In addition, optical fibres can be used in interstitial laser thermotherapy, as described for example in *"Focal therapy for prostate cancer"* Curr Opin Urol 18:269-274 by Thomas J. Polascik and Vladimir Mouraviev.

The use of diffuser and rotating fibres is described in *"Interstitial photodynamic laser therapy in interventional oncology"* Eur Radiol (2004) 14:1063-1073 by Thomas J.

Vogl, Katrin Eichler, Martin G. Mack, Stephan Zangos, Christopher Herzog, Axel Thalhammer, Kerstin Engelmann.

Again in these applications the optical fibres typically provide emissions only from the end of the fibre. Consequently, significant manipulation by the operator is again required to evenly irradiate the tumour of other portion of the subject under treatment.

SUMMARY OF THE PRESENT INVENTION

The present invention seeks to substantially overcome, or at least ameliorate, one or more disadvantages of existing arrangements.

In a first broad form the present invention seeks to provide a method of forming an optical fibre tip, the method including:
 a) roughening at least part of an end portion of the optical fibre; and,
 b) etching the roughed end portion to thereby form an optical fibre tip.

Typically a surface of the optical fibre tip has multiple facets.

Typically the facets are rounded with a concave form.

Typically each facet is for distributing incident radiation at multiple angles.

Typically the facets have a size in the region of 10 μm to 100 μm

Typically the optical fibre tip has a honeycomb surface structure.

Typically the method includes roughening the end portion by abrasion.

Typically the method includes abrading the end portion using a particle beam.

Typically method includes:
 a) rotating the end portion; and,
 b) exposing the rotating end portion to the particle beam.

Typically the particle beam includes particles of at least one of:
 a) aluminium oxide;
 b) cubic boron nitride;
 c) silicon carbide;
 d) silicon dioxide;
 e) zirconium oxide;
 f) zirconium dioxide;
 g) silicone carbide;
 h) corundum; and
 i) magnesium oxide.

Typically the particles have an average size of at least one of:
 a) between 25 and 100 μm; and
 b) approximately 50 μm.

Typically the particle beam is generated using a compressed gas.

Typically the gas is at least one of:
 a) air;
 b) nitrogen;
 c) carbon dioxide; and,
 d) a non-flammable gas.

Typically the gas has a pressure of approximately 2.8 bar.

Typically the method includes etching the end portion using an acid.

Typically the acid includes at least one of:
 a) hydrofluoric acid;
 b) a mixture of hydrofluoric acid and orthophosphoric acid; and,
 c) a mixture of hydrofluoric acid, orthophosphoric acid and a fluoride compound.

Typically the acid is in at least one of:
 a) a vapour phase; and,
 b) a liquid phase.

Typically the method includes etching the end portion for between 10 and 15 minutes.

Typically the method includes shaping the end portion.

Typically the method includes shaping the end portion prior to abrading the end portion.

Typically the method includes shaping the end portion so that the end portion tapers towards an end of the optical fibre.

Typically the method includes shaping the end portion into a conical shape.

Typically the method includes shaping the end portion by pre-etching the end portion.

Typically the method includes pre-etching the end portion using an acid.

Typically the method includes pre-etching the end portion for between 45 and 180 minutes.

Typically the method includes removing a polymer coating from the optical fibre to expose the end portion.

Typically the optical fibre is at least one of:
 a) a silica glass fibre;
 b) a fluoride doped silica glass fibre; and,
 c) a germanium doped silica glass fibre.

In a second broad form the present invention seeks to provide an optical fibre including a tip having a faceted surface structure.

Typically the facets are rounded and concave in form.

Typically each facet is capable of distributing radiation and collecting incident radiation at multiple angles.

Typically the facets have a size in the region of 10 μm to 100 μm

Typically the optical fibre tip has a honeycomb surface structure.

Typically the tip has a substantially conical shape.

Typically the tip tapers towards an end of the optical fibre.

In a third broad form the present invention seeks to provide apparatus for interaction with a part of a subject, the apparatus including:
 a) an optical system for at least one of generating or detecting radiation; and,
 b) an optical fibre coupled to the optical system at a first end, a second end of the optical fibre including a tip, at least part of the tip having a conical or faceted surface structure, that allows radiation to be emitted from or received via the tip at least partially in a direction perpendicular to an optical fibre axis.

Typically the optical fibre tip has a honeycomb surface structure.

Typically the optical fibre tip has a conical shape.

Typically the optical system includes a radiation source for generating radiation to be emitted from the tip.

Typically the optical system includes a sensor for sensing radiation received via the tip.

Typically the optical system includes:
 a) a first radiation source for emitting radiation of a first wavelength;
 b) a second radiation source for emitting radiation of a second wavelength; and,
 c) optical elements for optically coupling the first and second radiation sources to the first end of the optical fibre.

Typically the optical elements include an optical switch for selectively coupling the radiation sources to the optical fibre.

Typically the first radiation source is at least one of:
 a) a solid state laser;
 b) a gas laser;

c) a diode laser; and,
d) a light emitting diode.

Typically the first radiation source emits laser radiation of a first wavelength of between 650 and 670 inn.

Typically the second radiation source is at least one of:
a) a solid state laser;
b) a gas laser;
c) a high power diode laser; and,
d) a light emitting diode.

Typically the first and second radiation sources are formed from a diode laser operating in a low power mode for emitting the first radiation and in a high power mode for emitting the second radiation.

Typically the second radiation source emits laser radiation of a second wavelength of between 480 and 830 nm to activate a photosensitizer.

Typically at least one of the radiation sources is operated in a pulsed mode.

Typically the radiation source is operated in a pulsed mode to at least one of:
a) reduce accumulation of heat;
b) generate cavitation in fluids in which the fibre tip is placed;
c) generate shock waves in fluids in which the fibre tip is placed;
d) achieve ablation of dental hard tissues;
e) generate photo-acoustic effects;
f) improve a signal to noise ratio;
g) reduce heat dissipation from the apparatus; and
h) reduce power consumption.

Typically the apparatus includes a processing unit coupled to the optical elements for:
a) receiving light-induced fluorescence radiation; and,
b) measuring a level of bacteria in a cavity using the received radiation.

Typically the apparatus includes a processing unit for controlling at least one of the first and second radiation sources and an optical switch.

Typically the apparatus is for at least one of:
a) measuring a level of bacteria in a cavity using light-induced fluorescence; and
b) disinfecting the bacteria in a cavity using at least one of a photothermal, photoacoustic and photodynamic treatment;
c) exposing at least one of a cavity and a tumour to radiation;
d) for detecting optical fluorescence; and,
e) identification and treatment of bacteria in cavities of teeth.

Typically the cavities include root canals.

In a fourth broad form the present invention seeks to provide a method for interaction with a part of a subject, the apparatus including:
a) positioning an optical fibre tip adjacent at least the part of the subject, the optical fibre tip having a faceted surface structure that allows radiation to be emitted from or received via the tip at least partially in a direction perpendicular to an optical fibre axis; and,
b) using an optical system coupled to the optical fibre to at least one of generate or detect radiation, In a fifth broad form the present invention seeks to provide apparatus for identification and treatment of bacteria in cavities of teeth, wherein the apparatus includes:
a) a first radiation source for emitting radiation of a first wavelength;
b) a second radiation source for emitting radiation of a second wavelength; and,
c) optical elements for optically coupling the first and second radiation sources to the cavities for:
  i) for measuring a level of bacteria in the cavity using light-induced fluorescence; and
  ii) disinfecting the bacteria in the cavity using at least one of a photothermal, photoacoustic and photodynamic treatment method where a level of bacteria exists.

In a sixth broad form the present invention seeks to provide a method of identification and treatment of bacteria in cavities of teeth, the method including the steps of:
a) measuring a level of bacteria in the cavity canal using light-induced fluorescence;
b) disinfecting the bacteria in the cavity using a photothermal or photodynamic treatment method where a level of bacteria exists; and
c) re-measuring the level of bacteria in the cavity using light-induced fluorescence to provide feedback for the effectiveness of the treatment.

In a seventh broad form the present invention seeks to provide a method of modifying the surface structure of a material to thereby modify the optical properties, the method including:
a) roughening a surface of the material; and,
b) etching the roughed end surface such that the material has a faceted surface structure.

Typically the facets are rounded.

Typically each facet is for distributing incident radiation at multiple angles.

Typically the optical fibre tip has a honeycomb surface structure.

Typically the method includes roughening the surface by abrasion.

Typically the method includes abrading the surface using a particle beam.

Typically the particle beam includes particles of at least one of:
a) aluminium oxide;
b) cubic boron nitride;
c) silicon carbide;
d) silicon dioxide;
e) zirconium oxide;
f) zirconium dioxide;
g) silicone carbide;
h) corundum; and
i) magnesium oxide.

Typically the particles have an average size of at least one of:
a) between 25 and 100 μm; and
b) approximately 50 μm.

Typically the particle beam is generated using compressed gas.

Typically the gas is at least one of:
a) air;
b) nitrogen;
c) carbon dioxide; and,
d) a non-flammable gas.

Typically the gas has a pressure of approximately 2.8 bar.

Typically the method includes etching the surface using an acid.

Typically the acid includes at least one of:
a) hydrofluoric acid;
b) a mixture of hydrofluoric acid and orthophosphoric acid; and,
c) a mixture of hydrofluoric acid, orthophosphoric acid and a fluoride compound.

Typically the acid is in at least one of:
a) a vapour phase; and,
b) a liquid phase.

Typically the method includes etching the surface for between 10 and 15 minutes.

BRIEF DESCRIPTION OF THE DRAWINGS

An example of the present invention will now be described with reference to the accompanying drawings, in which:—

FIG. 10A is an example of the distribution of visible red light from a coaxial aiming beam for an unmodified optical fibre;

FIG. 10B is an example of the distribution of visible red light from a coaxial aiming beam for an optical fibre having a conical tip;

FIG. 10C is an example of the distribution of visible red light from a coaxial aiming beam for an optical fibre having a roughened conical tip;

FIG. 10D is an example of the distribution of visible red light from a coaxial aiming beam for an optical fibre having a roughened and etched conical tip;

DETAILED DESCRIPTION OF THE PREFERRED EMBODIMENTS

An example of a process for modifying the surface structure of a material to thereby modify the optical properties will now be described. For the purpose of this example, the process is used to produce an optical fibre tip as will now be described with reference to FIG. 1, and FIGS. 2A to 2C.

Figure 1:
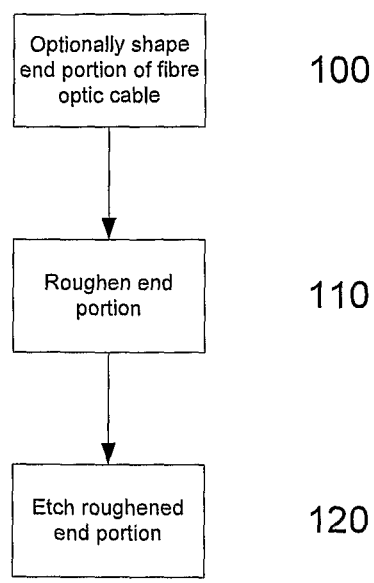
FIG. 1 is a flow chart of an example of a process for forming an optical fibre tip.
Figure 2A:
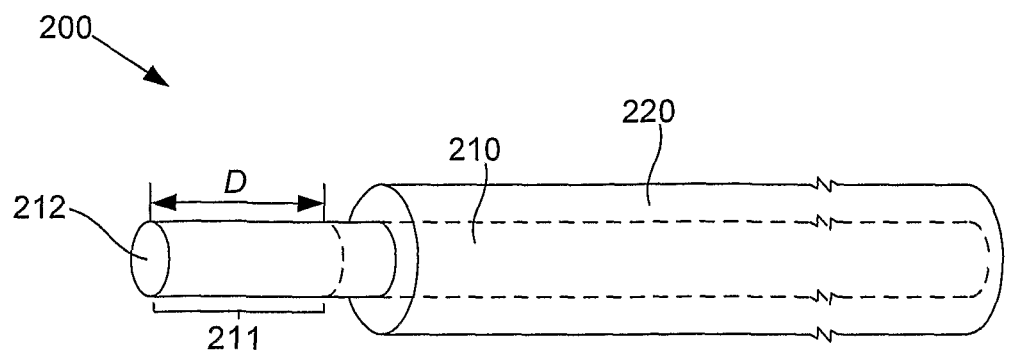
FIG. 2A is a schematic diagram of an example of an optical fibre having an end portion.

In this example, at step 100 an end portion of an optical fibre is optionally shaped. An example optical fibre 200 is shown in FIG. 2A. In this example, the optical fibre 200 includes a core material 210, such as a silica glass or the like, which may optionally be surrounded by a cladding 220, such as a protective polymer layer, or the like. In this example, the end portion 211 typically extends a distance D from an end 212 of the core 210. Typically the cladding 220 is removed to expose at least the end portion 211 and optionally for an additional part of the core 210 as shown.

Figure 2B:
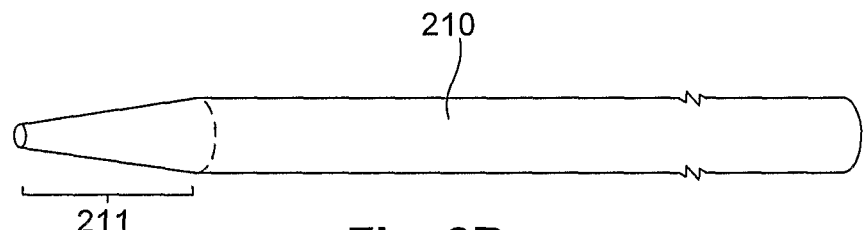
FIG. 2B is a schematic diagram of the optical fibre of FIG. 2A having a shaped end portion.

The shaping can be of any suitable shape, and is typically selected so as to maximise the amount of radiation impinging on an inner surface of the end portion 211. Accordingly, in one example, the end portion 211 is tapered to thereby provide a general conical shape, an example of which is shown in FIG. 2B. The shaping may be performed in any suitable manner such as polishing, grinding, etching, heat deformation, or the like, depending on the shape required.

At step 110 an outer surface of the end portion is roughened. The roughening may be performed in any suitable manner but in one example is performed by abrasion, for example using a particulate material entrained in a gas jet. Suitable particulate materials include aluminium oxide (alumina), cubic boron nitride, silicon carbide, silicon dioxide, zirconium oxide, zirconium dioxide, silicone carbide, corundum, and magnesium oxide. The gas may comprise compressed air, nitrogen, carbon dioxide or other non-flammable gases. In this example, the gas jet is directed towards the end portion such that the particulate material impacts on the surface thereby chipping and otherwise abrading the outer surface of the end portion 211, causing the surface to be roughened. The particles typically have a size between 25 μm and 100 μm and typically approximately 50 μm.

A more consistent effect can be achieved with a particle beam than using bonded abrasives such as in abrasive paper or grinding wheels, using either a manual technique or rotary polishing pad, and the risk of damage to the fibre is also reduced.

At step 120 the roughened end portion of the fibre optic cable is etched utilising an etching process, such as an acid etching treatment with a suitable acid. Suitable treatments include at least one of hydrofluoric acid; a mixture of hydrofluoric acid and orthophosphoric acid; and, a mixture of hydrofluoric acid, orthophosphoric acid and a fluoride compound, such as sodium fluoride, potassium fluoride or ammonium fluoride. The rate of etching and the shape achieved can be varied by altering the composition and temperature of the acid treatment, as well as by varying the exposure time for the acid etching treatment. Typically etching is performed for approximately 10 to 15 minutes The acid may be in a vapour phase or a like phase. In one example, the acid is applied to the fibre using a vapour method. In a further example, the acid treatment may be undertaken by immersion of the fibre in the etching liquid an acid-resistant polypropylene or Teflon container. In the most preferred method, etching is achieved by immersion of the fibre end in liquid through a second medium which alters the surface tension and angle of contact between the acid solution and the fibre tip. A suitable second medium is silicone oil, however other suitable acid-resistant materials can also be employed.

Figure 2C:
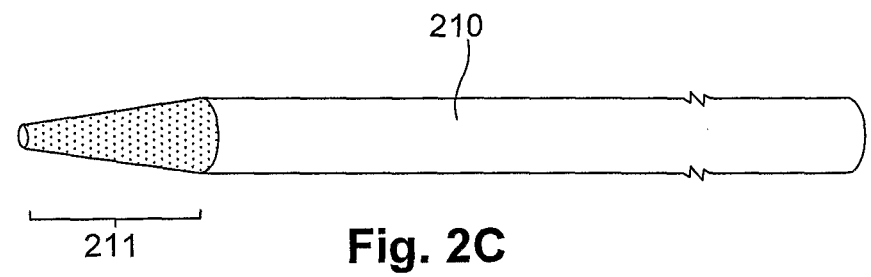
FIG. 2C is a schematic diagram of the optical fibre of FIG. 2B with the end portion having an etched roughened end portion.

The etching process typically enhances features in the roughened surface, thereby resulting in an irregular surface structure, as shown in FIG. 2C. In one example, the surface structure is a faceted or honeycomb surface structure having a number of facets that act to scatter radiation incident on the surface structure, as will be described in more detail below.

Scanning electro-microscope images example optical fibre end portions will now be described with reference to FIGS. 3A to 3D.

Figure 3A:
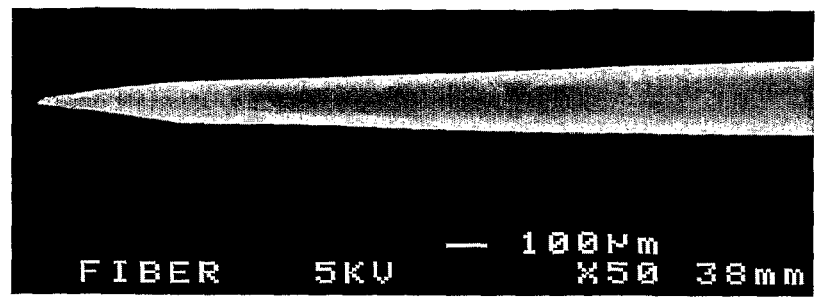
FIG. 3A is a scanning electron microscope image showing the surface topography of an example of an optical fibre having a conical shaped tip.

In the example of FIG. 3A, the end portion has been shaped at step 100 using an acid etch process, as will be described in more detail below. The image illustrates that the outer surface of the end portion 211 is typically smooth, following the shaping procedure.

Figure 3B:
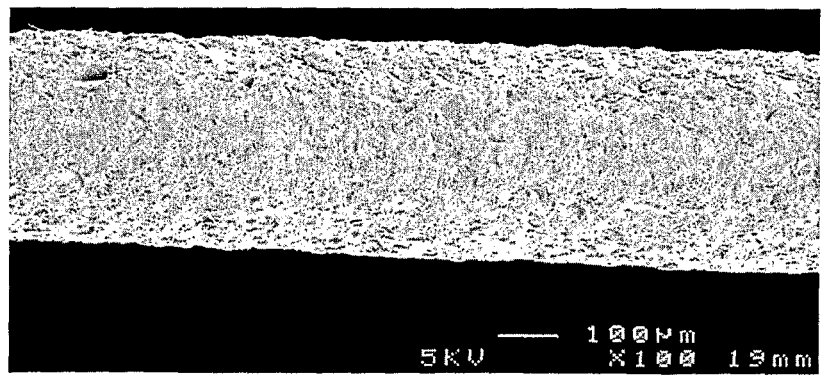
FIG. 3B is a scanning electron microscope image showing the surface topography of an example of an optical fibre having a roughened tip.

FIG. 3B shows an example in which the end portion of the optical fibre has been roughened, using a particulate abrasive. In this instance, the image shows that the end portion 210 has a roughened surface including small peaks and depressions.

Figure 3C:
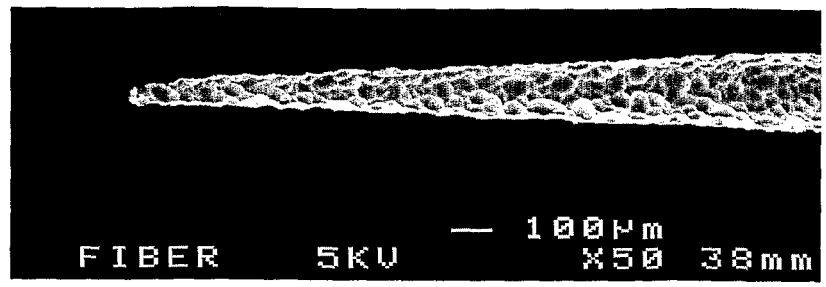
FIG. 3C is a first scanning electron microscope image showing the surface topography of an example of an optical fibre having a roughened and etched tip.
Figure 3D:
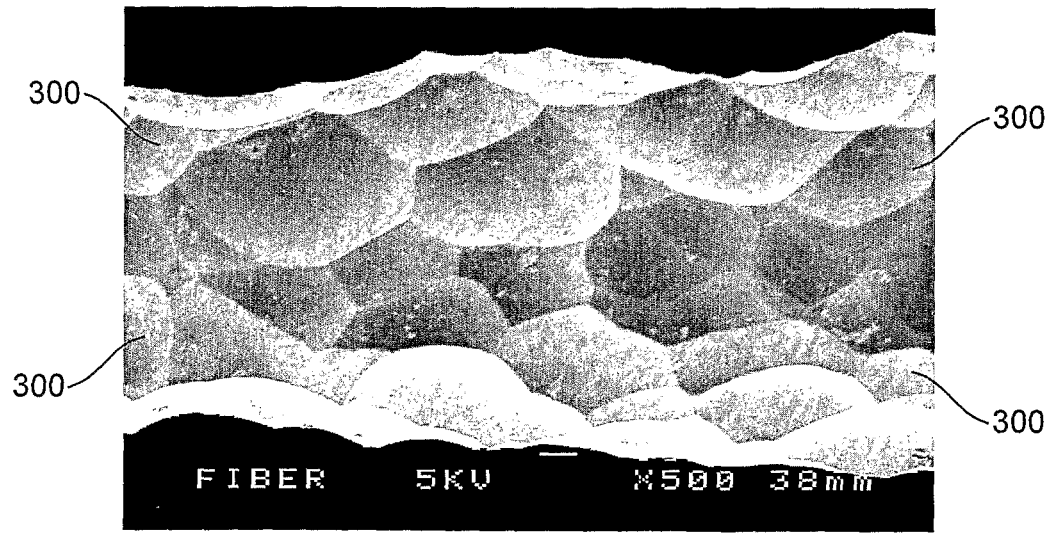
FIG. 3D is a second scanning electron microscope image showing the surface topography of an example of an optical fibre tip having a roughened and etched tip.

Following the etching process of step 120, the etched surface has an irregular surface structure having a number of facets 300, which form a generally honeycomb surface structure, as shown in FIGS. 3C and 3D. The honeycomb surface structure arises due to etching of the peaks and troughs in the roughened end portion surface, which enhances their relative size.

The size of the facets can be controlled by altering the particle size and/or the etching time. In this example, using particles having a size between 25 μm and 100 μm and etching time of between 10 to 15 minutes, the facets typically have a size in the region of 10 μm to 100 μm, and most preferably 50 μm. They have a regular concave form, and the overall topography of the treated surface is regular, even though the size of the individual facets vary from one to the next.

Figure 4A:
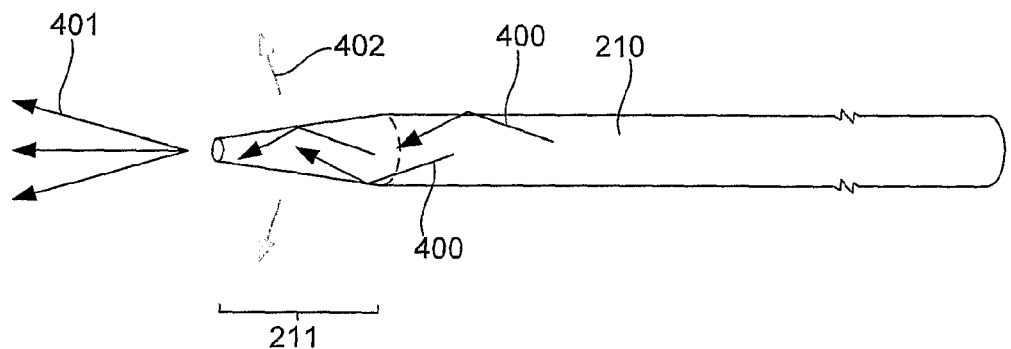
FIG. 4A is a schematic diagram of an example of radiation emission from the optical fibre of FIG. 3A.
Figure 4B:
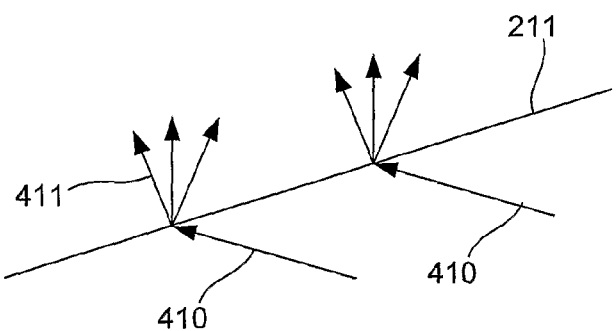
FIG. 4B is a schematic diagram of an example of radiation scattering by a roughened and etched surface.
Figure 4C:
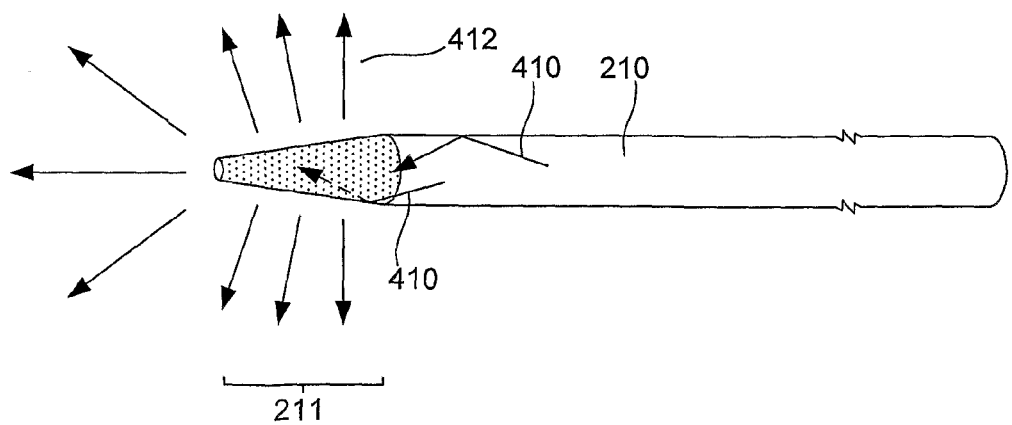
FIG. 4C is a schematic diagram of an example of radiation emission from the optical fibre of FIG. 3C.

The presence of the honeycomb surface structure enhances scattering of radiation from the surface of the end portion 211. As a result, the end portion emits a greater amount of radiation in a lateral direction (a direction extending generally perpendicularly to an axis of the end portion). An example of this is shown in FIGS. 4A to 4C. This surface modification also improves the ability of the fibre end to collect radiation, for example for use in diagnostic purposes. The regular overall shape of the surface assists for both transmitting and collecting light. In particular, the concave spherical form of the facets, and their size, optimises lateral dispersion and collection of both visible and near infrared light.

In the example of FIG. 4A, a smooth tapered end portion 211, resulting from a shaping of the end portion 211, is shown. In this example, radiation propagated by the core 210 is reflected from an inner surface of both the core 210 and the end portion 211, as shown by the arrows 400. As a result, the majority of radiation is emitted from the end 212 of the optical fibre, as shown by the arrows 401, with only very small amounts of radiation being emitted from the end portion 210 in a lateral direction, as shown by the arrows 402.

However, in the case of an optical fibre having a surface structure formed by roughening and etching, as shown in FIG. 4B, radiation 410 propagated by the core 210, is scattered from by the surface structure, as shown by the arrows 411. In particular, in this instance each facet of the surface structure distributes incident radiation at multiple angles, thereby leading to a broad scattering profile. This is assisted by the size of the facets being in the region of 10 μm to 100 μm, which optimises the scattering effect, thereby increasing lateral emissions. As a result, a much greater proportion of radiation is emitted from the end portion 210 in a lateral direction 412, as shown in FIG. 4C.

It is apparent from this that the presence of the surface structure increases the amount of radiation emitted laterally from the optical fibre. It will be appreciated that in a similar manner, if radiation impinges on the outside surface of the tip in a lateral direction, the surface structure enhances scattering of radiation which in turn increases the amount of radiation transmitted along the optical fibre. This is useful in detecting fluorescence, or the like.

The size and shape of the surface structures have an impact on the amount of scattering, and hence the amount of radiation emitted laterally from the fibre tip. Changes in the pattern of radiation emitted from the fibre tip affect the extent to which this energy induces one or more of the following actions:

the generation of cavitation, photo-acoustic effects and shock waves in fluids in which the fibre tip is placed;
ablation of hard tissues such as bone and tooth;
destruction of bacteria by photo-thermal actions
destruction of bacteria by photo-dynamic actions
reduce accumulation of heat;
generate photo-acoustic effects;
improve a signal to noise ratio;
reduce heat dissipation from the apparatus; and
reduce power consumption of the apparatus.

The surface structure likewise affects the ability of the fibre tip to receive radiation for diagnostic purposes. The size of the surface structures can be controlled by adjusting parameters relating to the roughening and etching process. The parameters that can be varied in the abrasion process include the abrasion time, abrading materials used, and the speed of impact of the abrading material. As specified above, etching parameters that can be adjusted include the etching time, etching method, etchant temperature, and the concentration and chemical composition of etchant used. The parameters will also be selected in accordance with the material forming the optical fibre. Accordingly, by appropriate control of the roughening and etching processes, this allows the proportion of radiation that is emitted in lateral as opposed to an axial direction, to be controlled.

Figure 5:
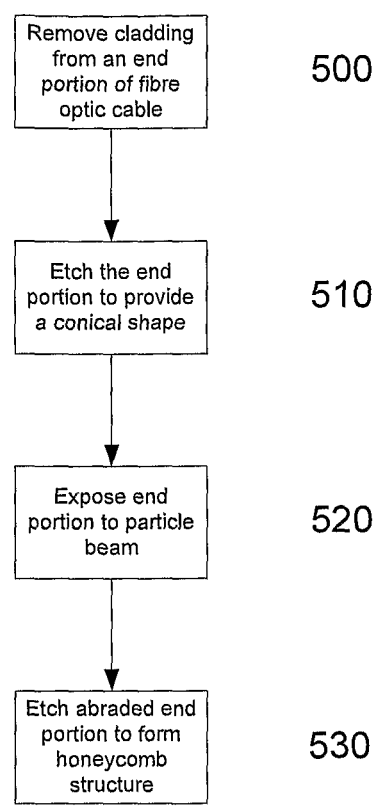
FIG. 5 is a flow chart of a second example of a process for forming an optical fibre tip.

A specific example of a process for forming a laterally emitting optical fibre tip will now be described with reference to FIG. 5.

Figures 6A, 6B, 6C:
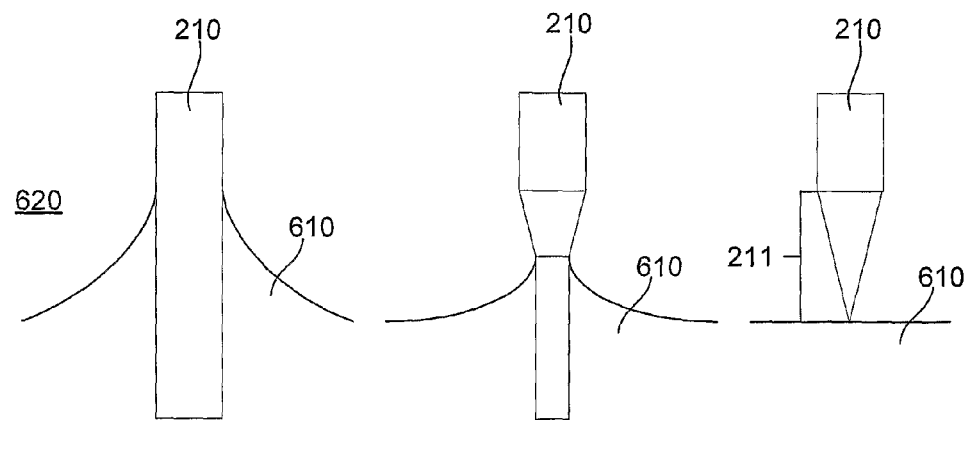
FIGS. 6A to 6C are schematic diagrams of an example of the process of etching an optical fibre to create a conical shaped tip.

At step 500, any cladding 220 is removed from the core 210, for at least the end portion 211, before the end portion 211 is etched to provide a conical shape at step 510. An example of the etching process is shown in FIGS. 6A to 6C.

In this example, an end of the optical fibre core 210 is immersed into a suitable etchant 610, such as hydrofluoric acid (HF) or other materials specified above. If pure HF is used, in one example, etching is achieved by providing the acid under an organic solvent layer 620, to reduce the quantity of HF vapours emitted into the ambient environment. The etchant wets the immersed fibre surface and forms an initial meniscus height due to surface tension at the interface between the optical fibre 210 and the etchant. As etching proceeds, the upward pulling force resulting from surface tension decreases due to the reduction of the fibre radius in contact with the etchant, as shown in FIG. 6B. Consequently, the meniscus height reduces progressively until the portion of the fibre below the solvent layer is completely etched, thereby forming the shaped end portion, as shown at 211 in FIG. 6C.

The fibre end may also be etched by placing it in HF vapour, and rotating it to achieve the desired surface shape. This variation of the etching method uses the vapour generated above a bath of HF in a negative pressure ventilation system.

After etching has been completed, the etched fibre is then removed from the etchant and may be treated to neutralise any remaining etchant, for example by rinsing successively with potassium hydroxide or sodium hydroxide solutions, sodium bicarbonate solutions, or the like, followed by water and finally acetone, ethanol, isopropanol or using volatile solvents to leave a dry surface.

Two variables that can be affected by variations in the etching process are the etching rate and shape of fibre. The etching rate can be influenced either by the temperature of the etchant, the concentration of the etchant, the physical composition of the etchant or the method of etching. The shape of the fibre can be affected by diameter of the fibre, density of etching solutions, concentration of etchant and temperature of etchant.

In one example, etching is performed using 50% hydrofluoric acid (HF), at 25 degrees Celsius, for between 45 and 180 minutes, to thereby produce the desired conical shape.

Figure 7:
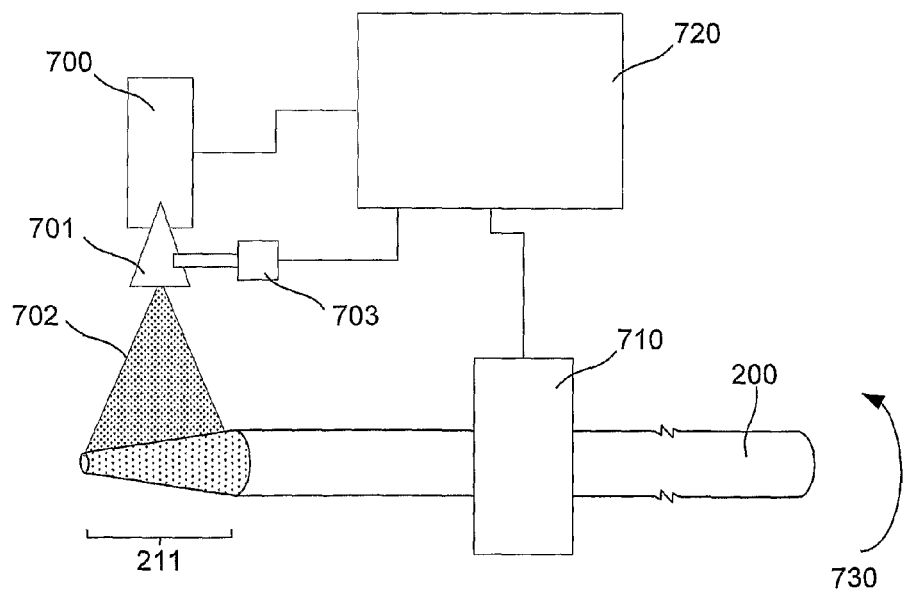
FIG. 7 is a schematic diagram of an example apparatus for roughening an optical fibre tip.

At step 520 the surface of the end portion is roughened using a particle jet, as will now be described with respect to FIG. 7.

In this example, a gas supply 700 having a nozzle 701 is used to generate a gas flow. Any suitable gas may be used, such as air, and in one example an air flow is generated using compressed air at a pressure of approximately 2.8 bar. However, alternative gases such as nitrogen, carbon dioxide or other non-flammable gases may be used. Particulate material can be injected into the gas flow from a particle source 703, so that particulate material becomes entrained in the gas flow to form a particle jet 702. Whilst any suitable particles may be used, in one example, the particles are aluminium oxide particles. However, alternatively particles of one or more of cubic boron nitride; silicon carbide; silicon dioxide; zirconium oxide; zirconium dioxide; silicone carbide; corundum; and magnesium oxide can be used.

The optical fibre 210 is positioned so that the end portion 211 is aligned with the particle jet 702. The optical fibre 210 may be held in position using a support such as a clamp 710. In one example, the clamp includes a drive to allow rotation of the optical fibre 210 about an optical fibre axis, as shown by the arrow 730.

In one example, a controller 720 is provided coupled to the gas supply 700, the particle source 703 and the clamp 710. The controller 720 can be any suitable form of controller, such as a processing system, FPGA or the like, that allows operation of the system to be controlled. Alternatively the system can be controlled manually.

In use, after positioning, the optical fibre 210 is rotated, and the particle jet 702 activated. This is typically performed for as long as required to produce the desired roughening of the structure, and in one example, is performed in 4 bursts of 0.5 sec each, whilst the optical fibre is rotated through 180 degrees.

Following roughening of the surface, at step 530, the roughened end portion can be etched a second time. Again, any suitable etchant such as hydrochloric acid, hydrofluoric acid, or the like may be used. In this example, the entire end portion 211 remains submerged, thereby ensuring even etching over the entire surface. In one example, etching is performed for shorter period of time, such as 10 to 15 minutes, depending on factors such as the temperature of the etching process, the composition of the optical fibre. Again etching is typically performed using 50% HF at 25 degrees Celsius.

Following etching, any remaining etchant is typically neutralised, allowing the resulting fibre to be used.

Etching can also be performed on fibres that are not shaped, and this can still result in a similar microscopic "honeycomb" surface structure providing improved lateral emissions, with the exception that the fibre tips had a parallel-sided shape rather than a conical design.

The resulting optical fibre tip can be used to illuminate the inside of cavities, such as tooth cavities and root canals. This can be used for a number of reasons, such as for performing ablation or photo-activated disinfection, as will be described in more detail below.

An example of use of the roughening and etching process, to demonstrate the effectiveness of this in allowing radiation to be emitted laterally from the optical fibre tip will now be described.

Lasers and Optical Fibres

For these examples, the optical fibres and the corresponding lasers used for the purpose of testing include an Nd:YAG laser (dLase 300, American Dental Laser, Fremont, Calif.) at 1.5 mJ/pulse, 20 Hz (3.0 W panel) with a 320 µm quartz glass fibre (WF 320 MDF, BioLitec, Winzelaer, Germany), an Er:YAG (KEY3, Model 1243, KaVo, Biberach, Germany) used at 200 mJ/pulse and 20 Hz (4 W), with a 400 µm (ISO 40) endodontic fibre, and an Er, Cr:YSGG laser (Waterlase MD, Biolase, Irvine, Calif.) used at a panel setting of 1.25 W and 20 Hz (62.5 mJ/pulse), delivered into a 400 µm endodontic fibre (MZ4).

Fibre Modifications

A total of 75 fibres (25 for each laser) were used. For each laser group these were further divided into 5 groups of five fibres each.

Group 1 were unmodified fibres, as provided by the manufacturer, to serve as controls.

Group 2 fibres were etched with 50% hydrofluoric acid using the etching technique described above for shaping the optical fibre. A silicon oil layer was placed over the HF to protect the fibre mounts from HF vapours. Etching was undertaken at 25 degrees Celsius, for durations ranging from 45 to 180 min. The appropriate etching times were determined from a pilot study in which the progress of etching was checked at 5 minute intervals using a microscope at a final magnification of 30×. The chosen endpoint was a conical pointed tip. Once etching was complete, the polymer coating was removed either by mechanical stripping or by dissolving it in hot concentrated $H_2SO_4$.

Group 3 fibres were etched using the same method, but had 2 mm of the polyimide coating removed before commencing etching.

Group 4 fibres had a 5 mm length of the polymer coating removed, and the exposed fibre then treated with a particle beam of medical grade 50 µm aluminium oxide (Microetcher ERC, Danville Engineering, San Ramon, Calif.) using compressed air at a pressure of 2.85 bar. The particle beam was applied in 4 bursts of 0.5 sec each whilst rotating the fibre tip 180 degrees during abrasion to achieve a consistent abrasive action.

Group 5 were modified in a 3-step protocol, by etching tube etching as in Groups 2 and 3, to obtain a conical configuration, then abrading the tip with the alumina particle beam, as in Group 4, and finally etching the fibre end once more. The second etching time was determined from a pilot study, and was 15 minutes for both WF 320 MDF fibres and Biolase fibres, and 10 min for KEY 3 fibres.

Before being further examined, the terminal 20 mm of all etched fibres in Groups 2, 3 and 5 was dipped in a saturated sodium bicarbonate solution to neutralize any residues of HF.

Figure 8A:
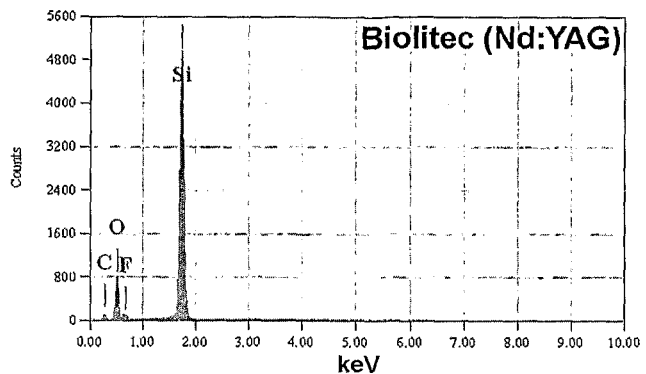
FIGS. 8A to 8C are elemental analytic graph of examples of optical fibres.
Figure 8B:
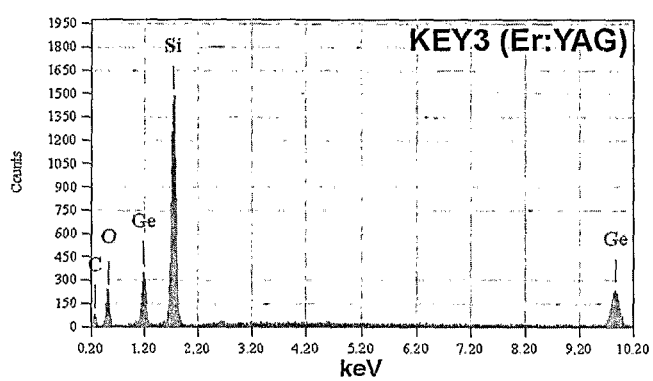
Figure 8C:
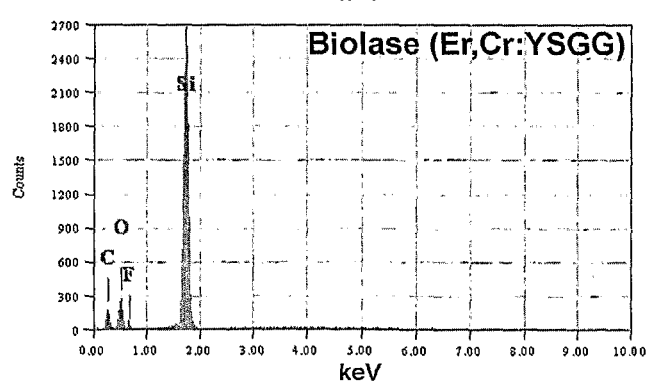

Elemental analysis of the three fibre types revealed differences in composition, with the Biolitec and Biolase fibres being a fluoride-doped silica glass and the KEY3 fibre a germanium-doped silica fibre. There was no change in fibre composition when samples were compared before and after etching with HF, examples of the compositions of the three different optical fibres described above are shown in FIGS. 8A to 8C.

The etching time required for Group 2 samples varied according to the fibre composition, with the depending on the type of fibre, with the germanium-doped fibres from the KEY3 laser requiring (mean±SD) 91 min (±9), versus 161 min (±6) and 174 min (±7) for the Biolitec and Biolase (fluoride-doped) fibres, respectively. The difference in etching times between fibre types was significant ($P<0.05$).

In the modified tube etching samples (Group 3), removal of the polyimide coating before etching reduced by one third the time required to obtain a conical end, in all fibre types. The etching times with the KEY3, Biolitec and Biolase fibres were 59 (±6), 106 (±7) and 130 (±7) min, respectively. There was, once again, a significant difference according to the fibre type ($P<0.001$). The reduction in etching time between tube etching and modified tube etching for matched samples in Groups 2 and 3 was significant ($P<0.0002$).

Resulting Tip Topography

Fibre tips were examined using a JEOL 6400 scanning electron microscope at 15 kV after sputtering with platinum. For elemental analysis, the fibres were sputter coated with carbon. Images were taken at a final magnification of 500× using a 6460 JEOL SEM for electron back scatter diffraction (EBSD) analysis at 30 kV.

The resulting scanning electron microscope images for a conical tip, a roughened tip, and honeycomb surface structure are shown in FIGS. 3A to 3D, as described above.

Simple etching with HF using the tube etching technique (Group 2) or modified tube etching technique (Group 3) both gave similar conical shaped fibre ends, with a typical final diameter of approximately 33μ, shown in FIG. 3A. Group 4 fibres treated with the particle beam showed a microscopically roughened surface, as shown in FIG. 3B. Fibres in Group 5 treated by etching, abrasion and further etching had a multi-faceted surface with a honeycomb-like appearance, as shown in FIGS. 3C and 3D.

Emission Measurements

The exit laser energy from the various fibres at fixed points in the forward direction (10 mm in front of the tip) and laterally (2 mm from the side of the tip) were measured with a power meter (Nova II, Ophir Optronics, North Andover, Mass.). T-tests were used to compare exit powers in forward and lateral directions between bare (Group 1) and modified tips.

Modified fibres showed reduced forward but enhanced lateral emissions when compared with unmodified fibres. ANOVA analysis with a post Tukey-Kramer multiple comparisons test showed statistically significant differences between the unmodified control fibre and the four types of modifications, for each type of fibre material used.

Figure 9A:
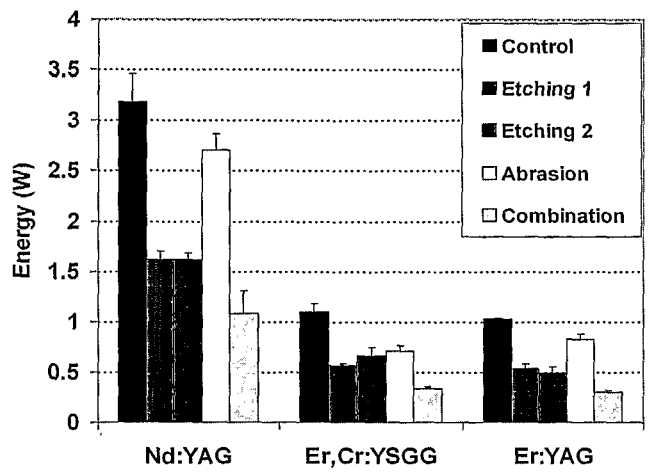
FIG. 9A is a graph of examples of forward emissions from a number of different optical fibre tips.
Figure 9B:
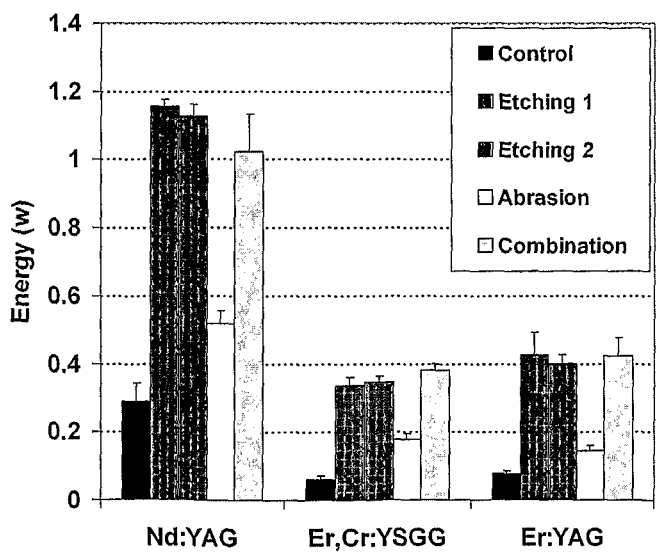
FIG. 9B is a graph of examples of lateral emissions from a number of different optical fibre tips.

In the forward direction, both conical shaped fibre tips, abraded tips and honeycomb tips showed reduced emissions, when compared with plain fibre ends. Differences between the two conical fibres (Groups 2 and 3) were not significant. The average reductions in forward emission for groups 2, 3, 4 & 5 were 49±1% (mean±SD), 47±7%, 23±11 and 68±4%, respectively, as shown in FIG. 9A. Fibre modifications gave substantial gains in lateral emissions, with groups 2, 3, 4 and 5 showing increases of 464±73%, 456±91%, 218±59% and 472±133%, respectively, as shown in FIG. 9B.

Angle of Divergence

Tracing the distribution of visible red light was undertaken using coaxial He—Ne laser (632.8 nm) (in the dLase 300 Nd:YAG system) or InGaAsP diode laser (635 nm) emissions (in the erbium systems). The distribution of visible red light was photographed on a grid using a stereomicroscope equipped with a digital camera, holding the fibre in direct contact to the gird. Angles of divergence were measured with aid of Image-J image analysis software (NIH, Bethesda, Md., USA).

Examples of the resulting emissions are shown in FIGS. 10A to 10D.

In the example of FIG. 10A, an unmodified fibre is shown, with radiation being emitted from the tip with a divergence of 15 degrees, as shown at 1000. The group 2 and 3 fibres, having the conical shaped tip, show a greater degree of divergence, but with the majority of the emissions in a forward direction, as shown at 1010 in FIG. 10B. In FIG. 10C, the roughened optical fibre demonstrates a wide degree of divergence, but with little side emissions 1020, whilst in FIG. 10D, the group 5 fibres having the honeycomb surface structure demonstrate 360 degree divergence with good lateral side emissions showing an emission profile along the length of the fibre and in a forward direction 1030.

The angles of divergence increased from 15 degrees in unmodified fibres (group 1) through to 360 degrees in the combination modification (group 5). The surface abrasion modification (group 4) gave less divergence forward of the tip than either of the etching modifications. Example measurements are shown in Table 1.

TABLE 1

| Laser | | Group 1 | Group 2 | Group 3 | Group 4 | Group 5 |
|---|---|---|---|---|---|---|
| Nd:YAG | Coaxial | 16.7 (0.8) | 103 (15) | 105 (18) | 360 (0) | 360 (0) |
| Biolase | guiding | 25.9 (0.9) | 165 (11) | 147 (20) | 360 (0) | 360 (0) |
| KEY3 | beam | 30 (0.7) | 156 (8) | 147 (7) | 360 (0) | 360 (0) |
| Nd:YAG | Thermal | 0 (0) | 101 (16) | 102 (16) | 0 (0) | 360 (0) |
| Biolase | paper | 0 (0) | 105 (1) | 102 (6) | 0 (0) | 360 (0) |
| KEY3 | imprint | 0 (0) | 108 (4) | 105 (6) | 0 (0) | 360 (0) |

Data are in degrees, and are means and standard deviations (N = 5).

The emission profile of the visible red coaxial aiming beam showed clearly the improved lateral emission of the modified fibre tips.

The distribution of infrared laser energy from the modified tips was further assessed using thermally sensitive paper. In this example, thermally sensitive white paper was used to record the emission profiles of the various fibre tips, with the tip kept parallel to and 2 mm above the surface of the thermal paper. To enhance absorption for the Nd: YAG laser, the non-sensitive side of the thermal paper was darkened with black printer ink. No enhancer was necessary with the erbium wavelengths.

Figures 11A, 11B:
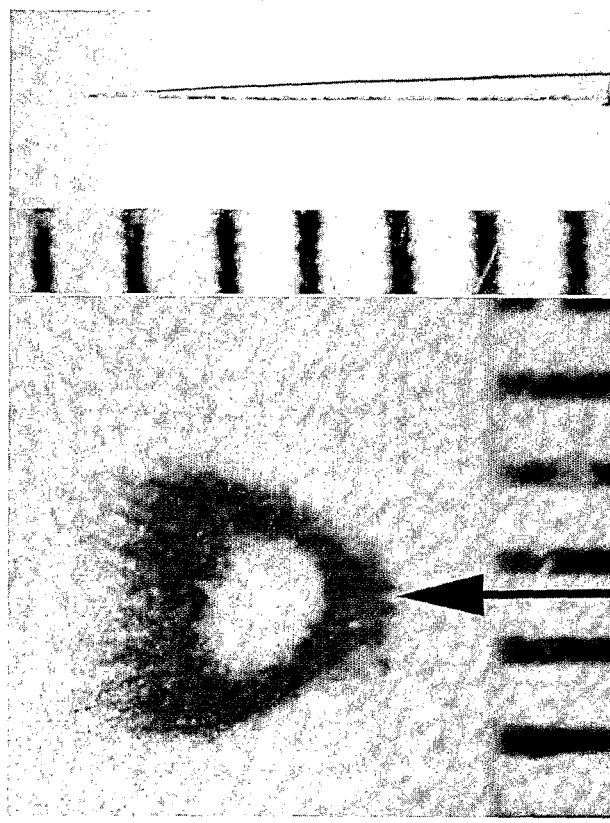
FIG. 11A is a photograph of an optical fibre tip having a conical shape.
FIG. 11B is a thermal imprint obtained using the optical fibre tip of FIG. 8A when used with the Nd:YAG laser.
Figures 11C, 11D:
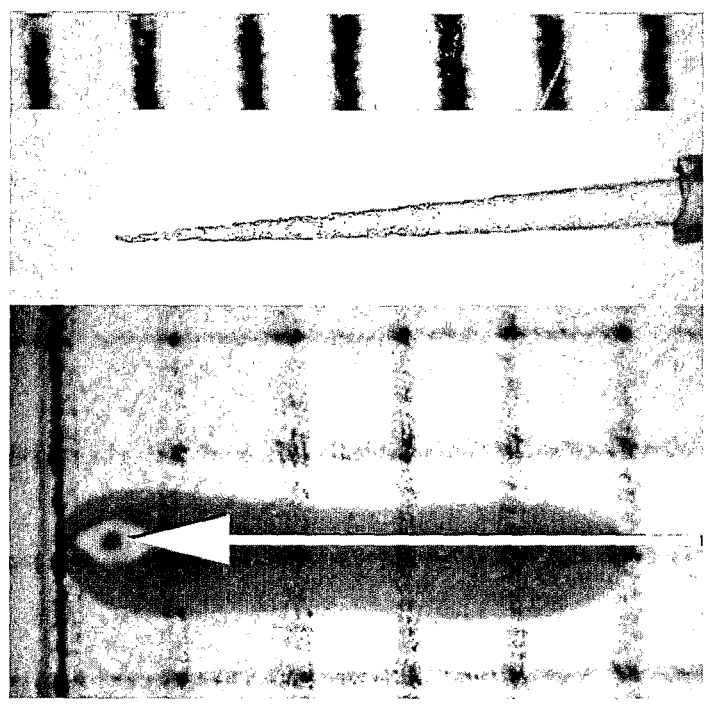
FIG. 11C is a photograph of an optical fibre tip having a roughened and etched conical tip; and, FIG. 11D is a thermal imprint obtained using the optical fibre tip of FIG. 8C when used with the Nd:YAG laser.

For the conical optical fibre of FIG. 11A achieved with the etching methods for groups 2 and 3, this results in a fan-shaped emission which was forward of the fibre terminus, as shown in FIG. 11B. In contrast, for the group 5 roughened and etched optical fibre shown in FIG. 11C demonstrates a broad lateral emission along the length of the modified tip, as shown in FIG. 11D. With the infrared laser emissions, the angle of divergence estimated from imprint on the thermal paper (with the fibre 2 mm distant from the paper) was less than seen by ray tracing of the visible red emissions of the aiming beam (where the fibre was in direct contact with the grid).

The results of this study indicate that modifications to existing optical fibres using relatively simple chemical and physical methods can improve the lateral emission of both visible and infrared laser energy. While conventional fibres gave a small divergence, etching of the fibre ends with hydrofluoric acid to create a conical tip (groups 2 and 3) increased this divergence to greater than 100 degrees in all fibre types, giving a fan-shaped beam. These conical tips could be useful for disinfection applications in the root canals of teeth and in periodontal pockets, however to obtain a uniform effect the fibre would need to be moved (e.g. withdrawn in a coronal direction whilst lasing) at a constant speed.

The combination of roughening and abrasion provides an irregular surface, and in one example provides a "honeycomb" surface topography with multiple facets and with excellent lateral emissions for visible, near infrared, and middle infrared wavelengths. Such fibres would be useful for ablative applications where placement in a root canal would achieve a relatively even effect along the length of the modified zone, since the gradation in size of the fibre tip is not dissimilar of that of a root canal. The even emission of visible red laser energy makes the honeycomb modification ideally suited for use in photo-activated disinfection, where 635 or 670 nm wavelength red light is used to excite tolonium chloride or methylene blue dyes, respectively, to achieve a disinfecting action within the root canal.

The roughening and etching combination provides an enhanced lateral emission profile compared to a simple surface abrasion modification. Surface abrasion only gives some lateral emissions with visible red laser light, but not with near or middle infrared wavelengths. This is not unexpected given the wavelengths of light used and the diffraction of this at the air-fibre boundaries of the modified fibre ends.

The above results therefore indicate that the honeycomb surface structure can provide dramatic improvements in lateral emissions from fibres, and in particular provide more effective lateral emissions than a normal conical configuration.

Using an optical system for at least one of generating or detecting radiation and an optical fibre coupled to the optical system at a first end, a second end of the optical fibre including a tip having a faceted surface structure, allows radiation to be emitted from or received via the tip at least partially in a direction perpendicular to an optical fibre axis. This can be used in interacting with parts of a subject, thereby assisting significantly in achieving even irradiation of the parts of the subject, or detecting fluorescence throughout a part of the subject.

This allows the optical fibres to be used in treating dental hard and soft tissue sites, including root canals and periodontal pockets, as well as tumourous tissues, or the like, as well as for detecting the presence of bacteria, tumours or the like, through fluorescence imaging, or the like.

The emission profile of the honeycomb fibre ends is of particular benefit for ablative applications in hard and soft tissues. Because of the strong lateral emissions, such tips would be useful for both endodontic procedures (such as ablation of debris, smear layer and dentine, from the walls of root canals), and periodontal applications, such as disinfection of periodontal pockets around teeth or dental implants. As the laser energy is emitted all along the length of the fibre end, a more even irradiation of the cavity can be achieved, when compared to the conventional method in which the fibre end is rotated and withdrawn.

An additional issue with plain fibres is their inherent risk of ledging, zipping or perforating the walls of curved root canals, a problem is overcome by side emitting fibre ends. In this regard, conical, abraded or honeycomb modified fibre ends would be safer to use than conventional bare tips.

Additionally, the optical fibres can also be used, for example, for photo-activated disinfection with visible red, near infrared, green or blue wavelengths.

Figure 12:
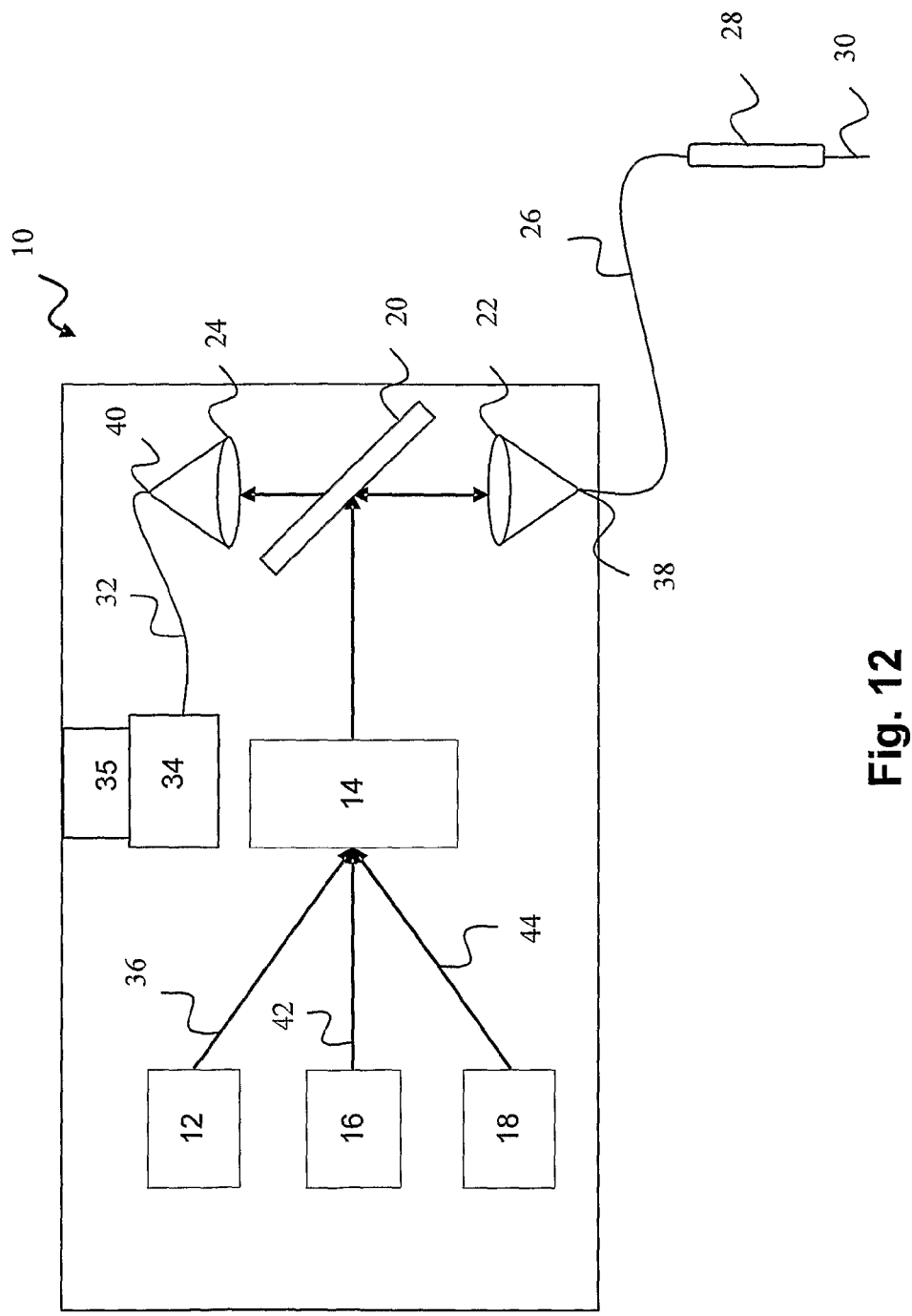
FIG. 12 is a schematic diagram showing an example of apparatus for treating bacteria.

An example of apparatus suitable for the identification and treatment of bacterial infections in cavities such as pulp chambers and/or root canals of teeth will now be described with reference to FIG. 12.

In one example, the apparatus 10 is a portable or handheld device, including a first light source in the form of a first laser or light emitting diode 12 optically coupled to an optical switch 14 through a suitable series of lensing elements or a graded refractive index terminal fibre. The apparatus 10 also comprises a second light source in the form of a second laser or light emitting diode 16 used for purposes of photodynamic, photo-acoustic or photothermal disinfection which is optically coupled to the optical switch 14. Alternative examples can also comprise one or more further light sources in the form of lasers or light emitting diodes 18 employed for disinfection as described further herein.

The apparatus 10 comprises optical elements in the form of a suitable dichroic mirror 20 and lenses 22, 24. Optical fibre 26 optically couples the lens 22 to a probe 28 having an optical element in the form of a flexible tip 30. Optical fibre 32 optically couples the lens 24 to a processing unit 34, although alternative couplings could be employed.

A processing unit 34 may be provided for assistance in performing the detection of bacteria. In one example, the processing unit 34 is coupled to an optical element for receiving light-induced fluorescence radiation and measuring a level of bacteria in the cavity using the received radiation. The processing unit 34 may also be adapted to control at least one of the first and second radiation sources and the optical switch. The processing unit 34 may be of any suitable form such as a suitably programmed computer system, custom hardware, or the like.

In one example, the processing unit 34 includes a long pass filter such that the visible red excitation wavelength is removed from the near infrared fluorescence signal. The processing unit 34 can be coupled to a display 35 which presents a visible indication of the presence of bacteria. An audible tone may also be produced.

The first laser or light emitting diode 12 emits laser radiation 36 of a first wavelength (650-670 nm) for measuring a level of bacteria in the pulp chambers and/or root canals of teeth using light-induced fluorescence. In one example, the first laser 12 is a 1.0 mW diode laser emitting laser radiation of a first wavelength of 655 nm, which has the benefit of providing eye protection by the human blink reflex. Optical switch 14 is set to allow the transmission of laser radiation 36 from the first laser 12 therethrough. Laser radiation 36 is reflected by the dichroic mirror 20 toward lens 22 where it is focused into an end 38 of optical fibre 26. The laser radiation 36 is transmitted through probe 28 and tip 30 into the site of the pulp chambers and/or root canals being investigated.

The emitted radiation causes fluorescence in microorganisms present in the pulp chambers and/or root canals of teeth, which is proportional to the degree of infection present. The laser fluorescence is collected by the flexible optical fiber tip 30 and is transmitted to lens 22 via probe 28 and optical fibre 26. Lens 22 collimates the fluorescence radiation, which is transmitted through dichroic mirror 20 to lens 24 where it is focused into an end 40 of optical fibre 32. The fluorescence radiation is directed into processing unit 34 where it is processed using the long pass filter to remove the excitation wavelength and to determine an indicator indicative of the level of bacterial infection, which can be output via the display 35. In one example, two indicators may be provided, including a first indicator that is a real time value that indicates the level of bacterial infection at the current position at which the active region of the optical fiber tip 30 is directed and a second indicator that is a peak value indicating the maximum level of bacterial infection at the site investigated.

Now that the pulp chambers and/or root canals having bacterial infection and the levels of infection in the chambers/canals have been determined, the bacterial infection is treated using the second laser 16, which emits laser radiation 42 of a second wavelength.

Optical switch 14 is set to allow the transmission of laser radiation 42 from the second laser 16 therethrough. Laser radiation 42 is reflected by the dichroic mirror 20 and focused by lens 22 into the optical fibre 26. The laser radiation 42 is transmitted through probe 28 and tip 30 into the site of the pulp chambers and/or root canals being treated.

In one example, the second light source 16 is a high power (100 mW) InGaAsP diode laser with a wavelength of between 630 and 670 nm. For photodynamic disinfection (PAD), an anti-bacterial solution containing the photosensitizer of choice is administered to the pulp chambers and/or root canals to be treated after the bacteria identification step and before the treatment step. The anti-bacterial solution is activated by the laser radiation 42 to kill the bacteria present via the process commonly known as photo-activated disinfection (PAD). Suitable photosensitizers which can be activated by visible red light which are well known to those skilled in the art comprise methylene blue, tolonium chloride, other phenothiazine derivatives, aluminium disulphonated phthalocyanine, haematoporphyrin hydrochloride, haematoporphyrin ester, arianor steel blue, crystal violet, azure chlorides, tryptan blue, azure blue dyes, azure compounds, and chlorins.

In one particular example, a photosensitizer in an aqueous medium, preferably at a concentration between 50 and 250 micrograms/mL, and most preferably at 150 micrograms/mL, is used. In addition to the photosensitizing dye, other components of the aqueous medium may comprise surfactants, buffers, salts for adjusting the tonicity of the solution, antioxidants, preservatives, and viscosity-adjusting agents (such as polyethylene glycol and the like). Preferably the aqueous medium will be at physiological pH and will be isotonic.

In alternative examples, treatment of the bacterial infection can be carried out using photo-thermal techniques instead of using the aforementioned photo-activated disinfection technique. The second light source 16 when employed for photo-thermal disinfection comprises one of the following lasers: Argon ion laser (488 or 514.5 nm), KTP/frequency doubled Nd:YAG laser (532 nm), GaAs or AlGaAs diode lasers (810, 830, 890, and 910 nm), Ho:YAG laser (2100 nm); Er:YSGG and ErCr:YSGG lasers (2780 and 2790 nm), or an Er:YAG laser (2940 nm).

Alternatively, such photo-thermal techniques can use the third light source 16 that emits pulsed laser radiation of a third wavelength at an energy sufficiently high to cause microscopic ablation of the dentine walls of the root canal, and the generation of photo-acoustic effects such as cavitation and shock waves, in addition to the disinfecting action. For example, the third light source 16 can be a Ho:YAG laser (2100 nm); Er:YSGG and ErCr:YSGG laser (2780 and 2790 nm), or an Er:YAG laser (2940 nm). This third light source would typically be operated in free-running pulsed mode with a pulse duration between 50 and 400 microseconds and a pulse energy of between 40 and 1000 milliJoules per pulse. Delivery of the laser radiation from the third light source 16 can be accompanied by a coaxial water mist spray to improve the photothermal ablative or cavitational cutting process from these infrared wavelengths and reduce deleterious thermal effects. A further variation is the use of a diode laser (810, 830, 910, 940, 980 nm) or the Nd:YAG laser (1064 mm), in which the generation of anti-bacterial photo-thermal actions is enhanced by ensuring that the fluid environment used in the root canal contains water to which has been added one or more an enhancing agents. Suitable agents include hydrogen peroxide and coloured dyes, such as tolonium chloride, methylene blue, and phenothiazine derivatives.

Once the bacterial infection in the pulp chamber/root canal has been treated, the remaining level of bacteria, if any, in the pulp chamber/root canal is re-measured using the first laser or light emitting diode 12 and the aforementioned light-induced fluorescence technique. This ensures that all of the bacterial infection has been treated and in the event that some bacteria remain in the pulp chamber/root canal, treatment using the photo-activated disinfection technique or one of the photo-thermal techniques can be repeated straight away.

Figure 13:
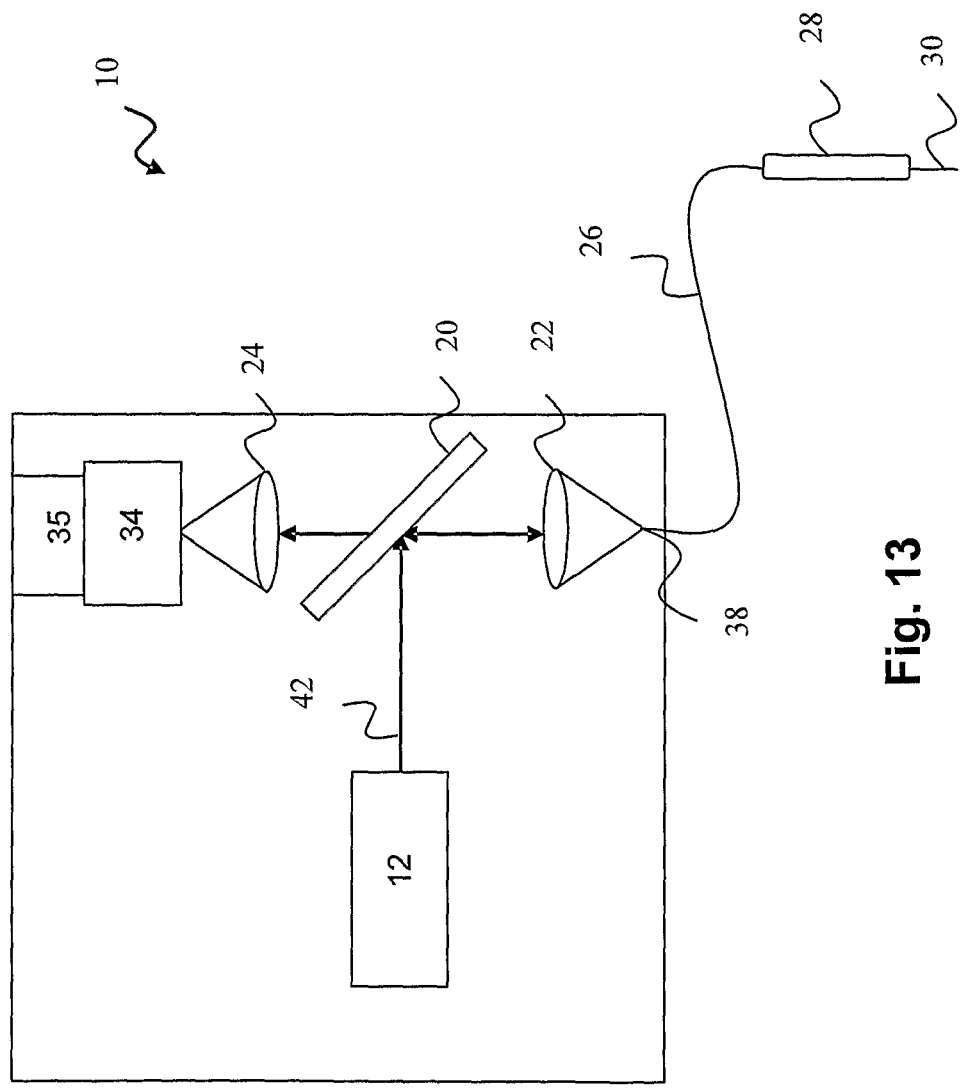
FIG. 13 is a schematic diagram showing a second example of apparatus for treating bacteria.

With reference to FIG. 13, an alternative example of the apparatus 10 comprises a light source 12 in the form of a diode laser both for measuring a level of bacteria in the pulp chamber/root canal using laser fluorescence and for disinfecting the bacteria where a level of bacteria exists. The apparatus 10 comprises the dichroic mirror 20, lenses 22, 24, optical fibre 26 optically coupling lens 22 to probe 28 having flexible tip 30 and processing unit 34 coupled to display 35, as shown in the first example. In this example, the output from lens 24 is received directly by processing unit 34. Optical switch 14 is also dispensed with since only a single light source 12 operated in at least two power modes is employed, thus simplifying the optical design considerably and consequently the size of the apparatus.

The diode laser 12 emits radiation at a wavelength of 655 nm and operates in a low power mode to measure the level of bacteria in the pulp chamber/root canal using laser fluorescence. The diode laser 12 then operates in a high power mode to disinfect the pulp chamber/root canal using a photodynamic treatment method. As with the previous example, the level of bacteria in the pulp chamber/root canal is re-measured using the diode laser operating in a low power mode following disinfection of the bacteria to provide feedback for the effectiveness of the treatment.

Figure 14:
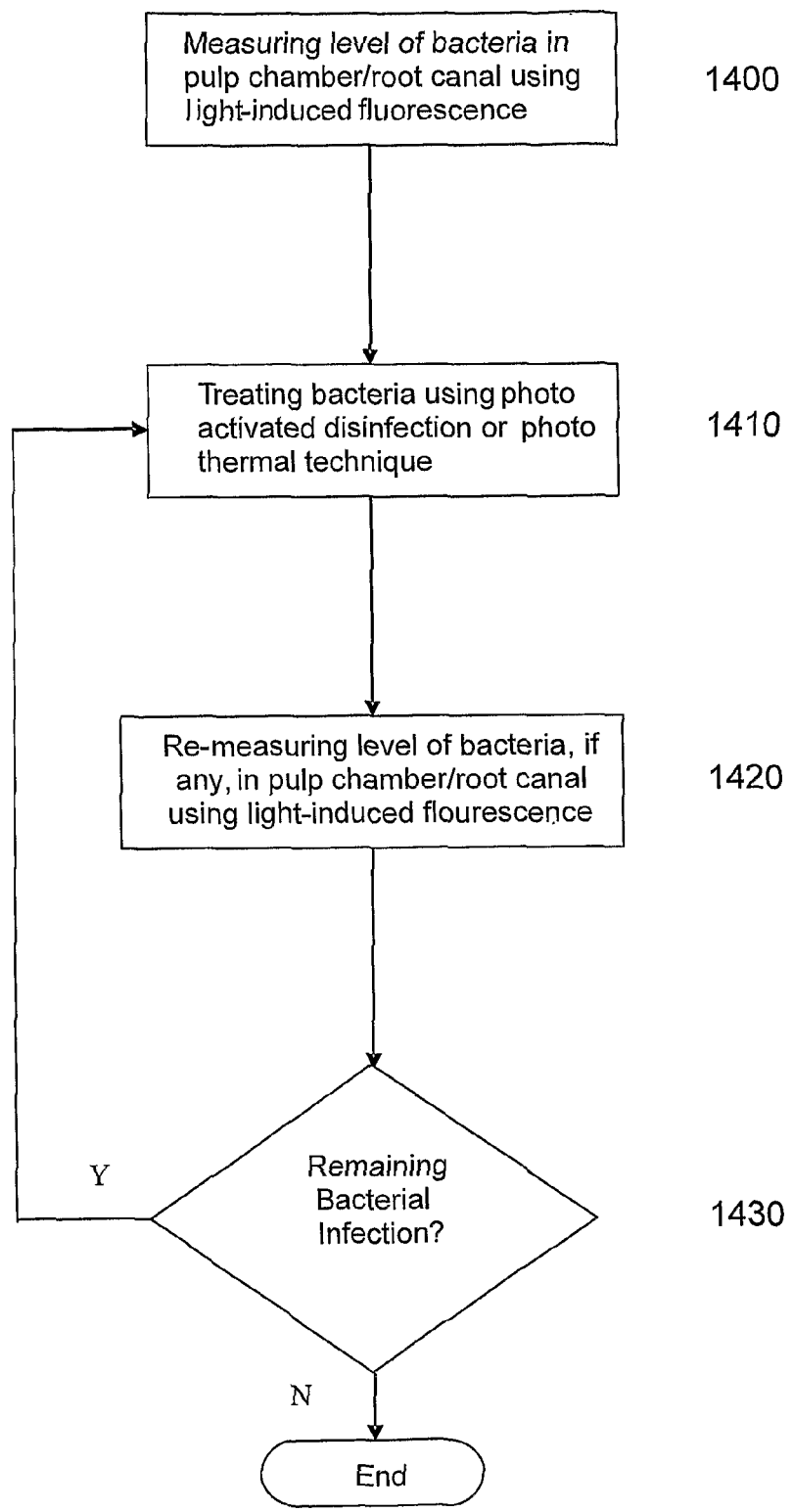
FIG. 14 is a flowchart illustrating a method of treatment of bacteria.

The method of treatment of bacteria in pulp chambers and/or root canals of teeth will now be described with reference to the flowchart shown in FIG. 14. The method includes, at step 1400, measuring a level of bacteria in the pulp chamber/root canal using the aforementioned apparatus 10 and the aforementioned light-induced fluorescence technique.

Where a level of bacteria exists, the method includes, at step 1410, treating the bacteria in the pulp chamber/root canal using one of the aforementioned treatment techniques. This can involve the aforementioned photo-activated disinfection technique or a photo-thermal technique. Where the photo-activated disinfection technique is used, an anti-bacterial solution is introduced to the pulp chamber/root canal before irradiating the pulp chamber/root canal with laser radiation from the treatment laser.

The method includes, at step 1420, re-measuring the level of bacteria, if any, in the pulp chamber/root canal using the aforementioned light-induced fluorescence technique using the first laser or light emitting diode 12. With reference to step 1430, if a bacterial infection remains in the pulp chamber/root canal, the treatment of step 1410 is repeated. If no bacteria remain, the treatment is complete and sealing of the pulp chamber/root canal can take place.

It will be appreciated that a range of different optical fibre tips can be used.

In one example, the optical element at the tip can comprise quartz glass, or where middle infared lasers are to be used for disinfection, a suitable transmissive material for both visible red and middle infrared light. Given that quartz glass partially attenuates light in the middle infrared wavelengths, suitable materials are quartz, gallium oxide, germanium oxide, zirconium fluoride aluminate, and hybrid fibres of germanium oxide with terminal low hydroxyl silica fibres. To ensure access to root canals, the fibre diameter is preferably between 150 and 600 micrometers, and most preferably 200 micrometers.

The fibre can have a cleaved end (such that the face is at right angles to the long axis of the fibre), and as such can function both for fluorescence detection and disinfection. Preferably, to improve the emission and collecting properties, the apical terminus (typically 1-5 millimeters) is modified in such a way that the red light used to elicit fluorescence is emitted in part from the side of the fibre. Modifications to the fibre terminus which achieve this purpose include Bragg gratings, alumina particle abrasion, and etching treatments.

In one particular example, the optical fibre tip has a honeycomb surface structure created using the above described techniques. It will be appreciated that this is particularly advantageous as it maximises lateral emissions of radiation from the optical fibre tip, thereby maximizing exposure of the bacteria to radiation. This in turn maximises bacterial detection and treatment, thereby providing an even further improved bacterial treatment process.

Accordingly, the above described apparatus 10 can therefore both identify the locations and levels of bacterial infection in pulp chambers/root canals of teeth and treat the bacterial infection in a single device. The portable or handheld apparatus also provides the user with alternative techniques for treating the bacterial infection. A high percentage of bacterial infection can be treated in a single treatment, especially more resistant Gram positive bacteria such as *Enterococcus faecalis*. The accurate identification and effective treatment of bacterial infections in teeth by the single apparatus enables rapid, one-stop treatments to be provided within a dental treatment setting.

Figure 15A:
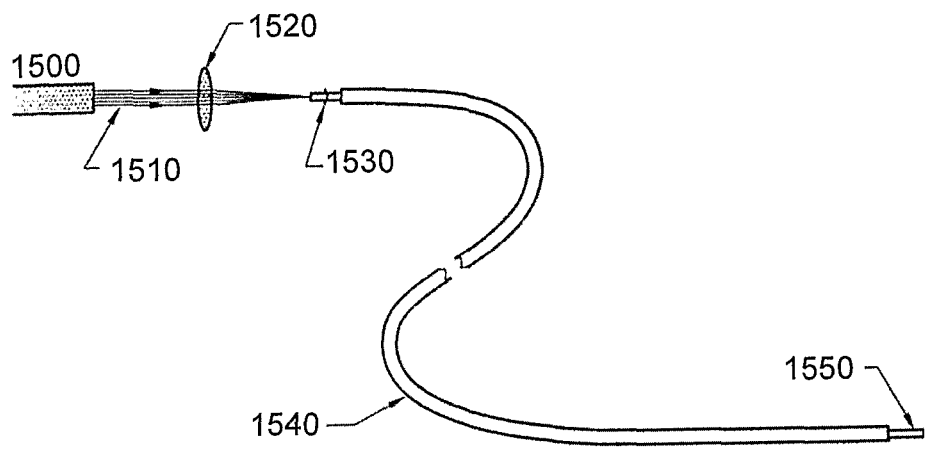
FIG. 15A is a schematic diagram of apparatus for exposing part of a subject to radiation.
Figure 15B:
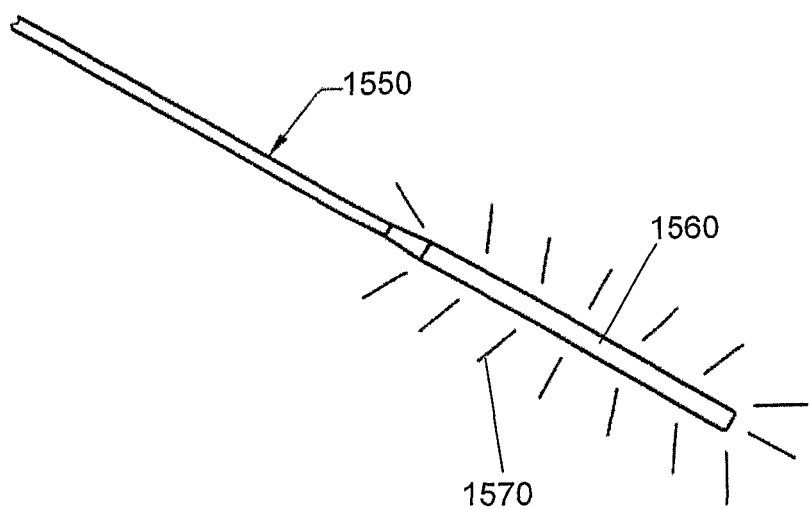
FIG. 15B is a schematic diagram of the optical fibre tip for exposing a part of a subject to radiation; and, FIG. 16 is a schematic diagram illustrating the effect of modifying the surface structure of a material.

It will be appreciated that in some applications it is only required to expose part of the subject to a single frequency of radiation, with no detection being performed. In this instance a more straight forward apparatus can be provided, as shown for example in FIGS. 15A and 15B.

In this example, the apparatus includes a radiation source 1500 for emitting radiation 1510. The radiation source is coupled to a first end 1530 of an optical fibre 1540, via an optical element 1520, such as a lens. The optical fibre includes a second end 1550, which has a tip 1560 having a modified surface structure to cause lateral emissions, as shown at 1570.

In addition to the above described dental applications, it will be appreciated that the optical fibre tips may be used in a range of different applications, in which a high degree of lateral emission is desired. Thus, for example, the apparatus could be used for treating tumours through the use of photodynamic therapy (PDT), or interstitial laser thermotherapy.

In this example, the tip is typically not conically shaped, but cylindrical, with a rounded end. This avoids the presence of a sharp point to the tip, which could damage tissue as the optical fibre tip is being moved into position within the subject.

In tumour therapy applications, the optical fibre tip 1560 is typically inserted into an incision in the tumour using a suitable micromanipulator. Once embedded, the radiation source 1500 is activated, allowing the inside of the tumour to be irradiated as known in the art. In contrast to prior art techniques however, the high degree of lateral emissions can ensure more even irradiation and hence improved treatment of the tumour.

It will also be appreciated that tumour detection can also be performed in a manner similar to bacterial detection in the dental application described above. In this instance, the tumour can be treated with a suitable fluorescing dye, allowing the fluorescence to be detected using a suitable sensing system, similar to that described above with respect to FIGS. 12 and 13.

In some situations, the optical fibre tip may not be insertable into the body part that requires treatment. In this instance, the optical fibre tip can be treated so that only part of the tip has a honeycomb surface structure. In one example, this can be achieved using the technique described above, but by only abrading one side of the optical fibre tip. In this example, whilst the entire tip may be etched, by only abrading one side of the tip, only the abraded side will have a modified surface structure, Consequently one side of the fibre tip will have an improved lateral emission profile, allowing this side of the tip to be positioned against the part of the body to be irradiated.

In addition to applications to optical fibres, the techniques can also be used to modify the surface structure of glass type materials for other applications. This can include any situation in which it is desired to alter the optical properties of a surface and in particular to modify the reflective and transmissive properties.

Figure 16:
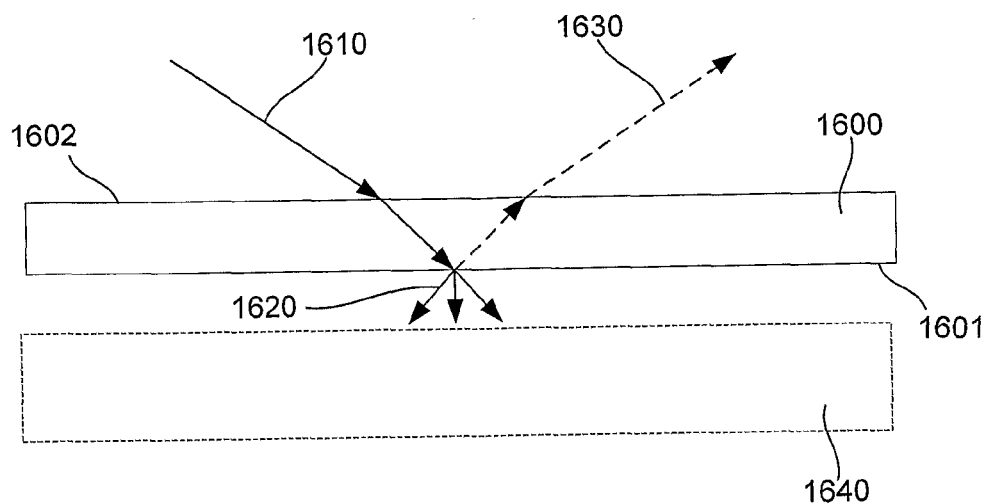

An example will now be described with reference to FIG. 16.

In this example, a sheet of material 1600 has a surface 1601 modified by roughening the surface of the material and then etching the roughed surface, so that the material has a faceted surface structure, and in one example as a honeycomb surface structure. It will be appreciated that parameters of the roughening and etching procedures can be varied depending on the physical properties of the material.

In this instance, if light is incident on the opposing surface 1602 of the material, as shown at 1610, the light will pass through the sheet and impinge on the surface 1601. The honeycomb structure scatters the radiation, resulting in emission of the radiation as shown generally at 1620. This reduces the occurrence of total internal reflection, which would otherwise cause radiation to be reflected from the sheet at 1630. By reducing total internal reflection, this maximises the amount of radiation passing through the sheet 1600, which is particularly useful in applications such as photovoltaic cells and solar water heating.

For example, this could be used in photovoltaic solar panels, which would typically include a photovoltaic material 1640 positioned adjacent the glass sheet 1600, thereby protecting the material 1640. In this arrangement solar radiation must pass through the glass panel 1600 in order to expose the photovoltaic material 1640. By reducing the reflectivity of the glass sheet 1600 this increases exposure of the photovoltaic material 1640 for a given amount of incident sunlight, thereby increasing the capacity of the solar panel to generate electricity.

It will be appreciated that additionally and/or alternatively the outer surface 1602 of the glass sheet 1600 could be treated, thereby further altering the transmissive properties of the glass panel.

The above described surface modification techniques can be applied to a range of materials having suitable properties, such as:
- silica glass;
- quartz;
- silica glass doped with lead oxide (10-60%)
- sapphire
- polycrystalline halide fibres such as AgBrCl
- chalcogenide glasses, such as As—S, As—Se, Ge—Ga—S, Ge—Ga—As—S, Ge—As—Se, Ge—Se—Te, As—Se—Te and Ge—As—Se—Te
- fluoride glasses such fluorozirconate, fluoraluminate, fluorindate, and fluorogallate.
- gallium oxide
- gallium oxide doped with lead oxide and bismuth oxide
- gallium oxide doped with heavier cations and anions, as described in U.S. Pat. No. 5,796,903.
- germanium oxide
- germanium oxide doped with lead oxide
- germanium oxide doped with zinc oxide (5-15%) and potassium oxide (5-15%)
- other heavy metal oxide glasses such as lead chloride, tellurium oxide—lead oxide, and tellurium oxide—zinc oxide The surface modification techniques are advantageously applied to optical fibre tips to thereby increase lateral emissions of radiation, but can also be applied to other situations in which it is desired to modify the optical properties of a material.

The techniques for detecting and treating bacteria in teeth can be applied in humans as well as in animals.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A method of forming an optical fiber tip, the method including:
   a) shaping an end portion of the optical fiber by etching the end portion;
   roughening at least part of the shaped end portion of an optical fiber by abrading the shaped end portion using a particle beam, and
   c) etching the roughened end portion to thereby form an optical fiber tip.

2. A method according to claim 1, wherein a surface of the optical fiber tip has multiple facets.

3. A method according to claim 2, wherein the facets are rounded with a concave form.

4. A method according to claim 2, wherein each facet is for distributing incident radiation at multiple angles.

5. A method according to claim 2, wherein the facets have a size in the region of 10 μm to 100 μm.

6. A method according to claim 1, wherein the optical fiber tip has a honeycomb surface structure.

7. A method according to claim 1, wherein the method includes:
   a) rotating the shaped end portion; and,
   b) exposing the rotating shaped end portion to the particle beam.

8. A method according to claim 1, wherein the particle beam includes particles of at least one of:
   a) aluminium oxide;
   b) cubic boron nitride;
   c) silicon carbide;
   d) silicon dioxide;
   e) zirconium oxide;
   f) zirconium dioxide;
   g) silicone carbide;
   h) corundum; and
   i) magnesium oxide.

9. A method according to claim 1, wherein the particles have an average size of at least one of:
   a) between 25 and 100 m; and
   b) approximately 50 m.

10. A method according to claim 1, wherein the particle beam is generated using a compressed gas.

11. A method according to claim 10, wherein the gas is at least one of:
    a) air;
    b) nitrogen;
    c) carbon dioxide; and,
    d) a non-flammable gas.

12. A method according to claim 10, wherein the gas has a pressure of approximately 2.8 bar.

13. A method according to claim 1, wherein the method includes etching the roughened end portion using an acid.

14. A method according claim 13, wherein the acid includes at least one of:
    a) hydrofluoric acid;
    b) a mixture of hydrofluoric acid and orthophosphoric acid; and,
    c) a mixture of hydrofluoric acid, orthophosphoric acid and a fluoride compound.

15. A method according to claim 13, wherein the acid is in at least one of:
    a) a vapour phase; and,
    b) a liquid phase.

16. A method according to claim 13, wherein the method includes etching the roughened end portion for between 10 and 15 minutes.

17. A method according to claim 1, wherein the method includes shaping the end portion so that the shaped end portion tapers towards an end of the optical fiber.

18. A method according to claim 1, wherein the method includes shaping the end portion into a conical shape.

19. A method according to claim 1, wherein the method includes shaping the end portion by etching the end portion using an acid.

20. A method according to claim 19, wherein the method includes shaping the end portion by etching the end portion for between 45 and 180 minutes.

21. A method according to claim 1, wherein the method includes removing a polymer coating from the optical fiber to expose the end portion.

22. A method according to claim 1, wherein the optical fiber is at least one of:
   a) a silica glass fiber;
   b) a fluoride doped silica glass fiber; and,
   c) a germanium doped silica glass fiber.

* * * * *